United States Patent [19]

Hamedi-Sangsari et al.

[11] Patent Number: 5,705,522
[45] Date of Patent: Jan. 6, 1998

[54] COMPOUNDS HAVING ANTI-INFLAMMATORY AND ANTI-VIRAL ACTIVITY, COMPOSITIONS OF THESE, ALONE AND IN COMBINATION WITH REVERSE TRANSCRIPTASE INHIBITORS

[75] Inventors: Farid Hamedi-Sangsari; Fabienne Nugier; Thierry Vallet, all of Lyons; Jacques Grange, Oullins; Jorge Vila, Lyons, all of France

[73] Assignee: Compagnie de Developpement Aguettant S.A., Lyons, France

[21] Appl. No.: 600,525

[22] Filed: Feb. 13, 1996

Related U.S. Application Data

[63] Continuation-in-part of Ser. No. 528,879, Sep. 15, 1995.

[51] Int. Cl.$^6$ .......................... A01N 43/36; C07D 205/10; C12P 21/02; C07C 209/28
[52] U.S. Cl. .......................... 514/423; 514/425; 514/426; 548/952; 435/69.2; 562/553; 562/577; 562/582
[58] Field of Search .......................... 548/952; 514/423, 514/425, 426; 435/69.2; 562/553, 577, 582

[56] References Cited

U.S. PATENT DOCUMENTS

| | | |
|---|---|---|
| 4,861,759 | 8/1989 | Mitsuya et al. . |
| 5,254,539 | 10/1993 | Mitsuya et al. . |
| 5,571,839 | 11/1996 | Vila et al. . |

FOREIGN PATENT DOCUMENTS

| | | |
|---|---|---|
| 0 206 497 | 12/1986 | European Pat. Off. . |
| WO 87/01284 | 3/1987 | WIPO . |
| WO 90/13291 | 11/1990 | WIPO . |
| WO 93/21218 | 10/1993 | WIPO . |
| WO 94/27590 | 12/1994 | WIPO . |
| WO 95/17875 | 7/1995 | WIPO . |

OTHER PUBLICATIONS

PCT/ISA/220 Notification of Transmittal of the International Search Report or Declaration dated Dec. 18, 1996.
International Search Report dated Dec. 10, 1996.
Blodgett, et al., "Specific Cleavage of Peptides Containing an Aspartic Acid (β-hydroxamic Acid)", J. Am. Chem. Soc., 1985, 107, 4305–4313.
J. Org. Chem., vol., 42, No. 10, (1977), pp. 1750–1761, Miller et al., "The Chemistry of a Method for the Determination of Carboxyl-Terminal Residues in Peptide".
J. Am Chem. Soc. 1985, vol. 107, pp. 4305–4313 "Specific Cleavage of Peptides Containing an Aspartic Acid (β–Hydroxamic Acid) Residue", Blodgett et al.
CDC (Center for Disease Control), MMWR, 30: 305–308.DC, (1981).
Barre–Sinoussi F. et al., Science, 220: 868–870 (1983).
Fauci AS., Science, 239, 617–622, (1988).
Fauci AS., Science, 262: 1011–1018, (1993).
Zack J.A. et al., Cell, 61, 213–222, (1990).
Bukrinsky M.I. et al.; Science, 254, 423–427, (1991).
Schnittman S M. et al., Science, 245, 305–308, (1989).
Fox CH. et al., J. Infect Dis; 164, 1051–1057, (1991).
Hirsch MS, et al., New Engl. J. Med. 328, 1686–1695, (1993).
Pauwels, R. et al., J. Virol. Methods, 20, 309–321 (1988).
Yarchoan et al., New Engl J. Med, 321, 726–738 (1989).
Chow et al., Nature, 361, 650–654 (1993).
Lori et al., Science, 266: 801–805 (1994).
McMillan R., et al, TIPS, Aug. 1992, vol. 13, pp. 323–330.
Merck Index 10, 8741, 8744, 8745, (1983).
M. Bodansky, A. Bodansky, The Practice of Peptide Synthesis, 125 (1984).
Vogel, Text–Book of Practical Organic Chemistry, 371, 375–377 and 840, (3rd. edition, 1957).

*Primary Examiner*—Johann Richter
*Assistant Examiner*—Jane C. Osweicki
*Attorney, Agent, or Firm*—Bell, Boyd & Lloyd

[57] ABSTRACT

A new family of compounds having anti-inflammatory, anti-viral, and brocho-dilating activity having the following linear and cyclic formulas:

$$HONR^4\text{—}(CO)\text{—}(CH_2)_n\text{—}CH(NHR^2\text{—}CO\text{—}R^1)\text{—}C(R^3)(OH)(=O)$$

I (linear form)

$$\text{cyclic structure with } R^2\text{—N—C(=O)—R^1, (CH}_2)_n, R^3, \text{N—OH}$$

II (cyclic form)

and compositions of these, which alone, and in combination with reverse transcriptase inhibitors thereby resulting in an additive or synergistic effect, are useful in inhibiting or suppressing viruses including those exhibiting retroviral replication, or in treating viruses including a retrovirus such as HIV in a human cell population and methods of using these compositions, compounds, and salts thereof.

42 Claims, 13 Drawing Sheets

Microfiche Appendix Included
(4 Microfiche, 214 Pages)

COMPOUNDS HAVING ANTI-INFLAMMATORY AND ANTI-VIRAL ACTIVITY, COMPOSITIONS OF THESE, ALONE AND IN COMBINATION WITH REVERSE TRANSCRIPTASE INHIBITORS

CROSS REFERENCE TO RELATED APPLICATIONS

This application is a continuation-in-part of Ser. No. 08/528,879 filed Sep. 15, 1995, the entire contents of which is herein incorporated by reference.

BACKGROUND OF THE INVENTION

1. Field of the Invention

The present invention relates to a new family of compounds having anti-inflammatory, anti-viral, and broncho-dilating activity which, additionally, in combination with a reverse transcriptase inhibitor results in an additive or synergistic effect which is useful in inhibiting or suppressing retroviral replication or eliminating a retrovirus in a human cell population.

2. Description of Related Art

The expression "Acquired Immuno-Deficiency Syndrome" (AIDS) was first used in 1981 to describe a state of cellular immune deficiency in homosexuals, characterized by the appearance of opportunistic infections and Kaposi's Sarcoma evolving very aggressively [CDC (Center for Disease Control), MMWR, 1981; 30: 305–308.DC]. In 1983, a retrovirus since called HIV (Human Immunodeficiency Virus) was isolated among AIDS patients (Barré-Sinoussi F, et al., *Science*, 1983; 220: 868–871).

Over the past several years, researchers and clinicians have gained considerable experience in studying and caring for individuals infected with HIV throughout the often prolonged course of HIV disease and AIDS. On the basis of this experience, it has become clear that the pathogenic mechanisms underlying HIV infection and disease are not unidimensional, but rather are extremely complex (Fauci AS, *Science*, 1988; 239: 617). Any attempt to design a comprehensive therapeutic strategy for HIV disease must take this fact into account (Fauci, *Science*, 1993; 262: 1011–1018).

A number of 2'-3'-dideoxynucleosides have been found to be useful for the treatment or prophylaxis of retroviral infections and especially HIV and AIDS. Examples of such materials include: 2',3'-dideoxy-cytosine (ddC); 2',3'-dideoxyadenosine (ddA); 2',3'-dideoxyguanosine (ddG); 2',3'-dideoxy-inosine (ddI), 2',3' dideoxy-thymidine (ddT), 3'-azido-2',3'-dideoxythymidine (AZT), 2'deoxy-3' thiocytidine (3TC) and 2',3'-didehydro-3'-deoxythymidine (d4T).

However, there still remains a need for more effective treatment for the suppression of retroviruses and, in particular, the prevention and/or inhibition and/or suppression of HIV. Unfortunately, currently available agents are only partially effective in inhibiting viral replication and spread; any such effect being transient, and completely ineffective in eliminating the virus (Hirsch MS, et al., *New Engl. J. Med*, 1993; 328: 1686–1695). Clear cut, but limited, benefit is seen when 3'-azido-2',3'-dideoxythymidine or azidothymidine (AZT) is given to a patient with advanced HIV disease, and the benefits of early intervention are usually only temporary and do not result in significant long-term advantages with regard to the course of disease and death. (Concorde Coordinating Committee, *The Lancet* 1994; 343: 871–881).

Effective anti-HIV chemotherapy may depend on meeting at least the following three criteria. Firstly, treatment should be capable of complete virus suppression to avoid drug failure (Richman D., *Aids Res. Hum. Retrovir.*, 1994; 10: 901–905). Secondly, new antiretroviral agents should include compounds with less toxicity and antiviral activity greater than AZT. Thirdly, there is a need for drug combinations which provide an additive or synergistic effect and decrease the probability of drug resistant isolates.

After entry of the HIV virus into cells and uncoating of the HIV particle, reverse transcription of the viral RNA genome into DNA replicas occurs. Among several forms of unintegrated viral DNA (now containing the long repeats [LTRs], at both the 5' and the 3' ends), only the two-LTR linear forms can integrate into the host genome. Such a process appears strictly dependent upon cell activation/replication of T lymphocytes, although "resting" T cells are clearly susceptible to HIV infection. (Zack J. A, et al., *Cell*, 1990; 61: 213–222). Furthermore, part of the reverse transcription process also can occur in unactivated T cells, a process that results in the accumulation of incomplete DNA molecules, which may persist for several hours and remain capable of being integrated into the host genome if the cell undergoes sufficient activation (Zack J. A, et al., *Cell*, 1990; 61: 213–222). Therefore, infected "resting" CD4+T lymphocytes can be considered a transient viral reservoir in infected individuals (Bukrinsky M. I, et al. *Science*, 1991; 254: 423–427), and a high HIV burden has also been observed in lymphoid tissue as intracellular virus in latent form (Embretson J, et al., *Nature*, 1993; 362: 359–362).

A new family of compounds has been found to be useful alone and in combination with reverse transcriptase inhibitors in inhibiting retroviral replication and eliminating retroviruses in human cell populations and in particular in HIV-infected resting human lymphocytes. Included in this family are the new compounds D-acetamido-N-hydroxy succinamic acid; D-acetamido-N-hydroxy succinimide; D-trifluoroacetamido-N-hydroxy succinamic acid; D-trifluroacetamido-N-hydroxy succinimide; and salts thereof. Furthermore, these compounds have been found to have the advantage over other antiviral agents in that they have very little, if any, cytotoxic or cytostatic activity, which gives them a broad therapeutic index when used for their antiviral effect in an infected cell population.

Additionally, these compounds have been found to be useful in treating asthma and have a therapeutic potential as anti-inflammatory agents and broncho-dilating agents for treating a range of diseases which includes arthritis and asthma-like diseases. R. M. McMillan and E. R. H. Walker in "Designing Therapeutically Effective 5-Lipogenase Inhibitors" Elsevier Science Publishers Ltd., TIPS, Vol. 13, (August, 1992) pp. 323–330 disclose that there are three classes of 5-lipoxygenase inhibitors: "redox" inhibitors, "non redox" inhibitors, and "iron ligand" inhibitors and that hydroxamate compounds are powerful iron ligand inhibitors.

Although not being bound by theory, it is expected that by blocking the synthesis of leukotrienes known to be powerful broncho-constrictor agents, this new family of hydroxamate compounds has therapeutic potential both as an anti-inflammatory agent and as a broncho-dilating agent, specifically in a range of diseases which includes arthritis and asthma. It is to be noted that all references cited herein are expressly incorporated, in total, by reference thereto.

SUMMARY OF THE INVENTION

The present invention relates to a new family of compounds having anti-inflammatory, broncho-dilating and antiviral activity. Inter alia, these compounds, including D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof in combination with a reverse transcriptase inhibitor (RT inhibitor) result in an additive or synergistic effect which is useful in inhibiting or suppressing retroviral replication or eliminating a retrovirus including HIV in a human cell population.

Specifically, the present invention relates to a method of preventing and/or inhibiting the spread of viruses and/or eliminating viruses including HIV (HIV-1 and HIV-2), HTLV-1, HTLV-2, SIV, HSV, HBV or HCV by exposing a cell population, including cells infected by a retrovirus such as, for example, HIV, to any one of a new family of compounds including D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof.

More specifically, the present invention relates to a method of preventing and/or inhibiting the spread of viruses and/or eliminating viruses including HIV (HIV-1 and HIV-2), HTLV-1, HTLV-2, SIV, HSV, HBV or HCV by exposing a cell population, including cells infected by a retrovirus such as, for example, HIV, to an additive or synergistic combination of a reverse transcriptase inhibitor (or more than one reverse transcriptase inhibitor) and any one of a new family of compounds including D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof. Additionally, the present invention encompasses the treatment of HIV-infected and AIDS patients with an additive or synergistic combination of a reverse transcriptase inhibitor and any one of a new family of compounds including D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof, in order to prevent and/or inhibit the spread of and/or eliminate HIV in these patients.

In a preferred embodiment of the present invention, the reverse transcriptase inhibitors include dideoxynucleosides, such as, for example, AZT, ddC, ddA, ddG, ddI, ddT, 3TC and d4T. In particular and in a more preferred combination of the present invention, it has been found that an additive or synergistic combination of DANHSA or DTFANHSA and any one of ddI, AZT, ddC or 3TC can be formed which is especially effective in inhibiting HIV production and eliminating HIV.

Another preferred embodiment of the invention encompasses a composition including a pharmaceutical composition comprising an additive or synergistic combination of DANHSA or DTFANHSA and any one of AZT, ddC, ddA, ddG, ddI, ddT, 3TC and d4T, or most preferred ddI, AZT, ddC or 3TC. Other preferred embodiments include the combination of two compositions comprising DANHSA or DTFANHSA as a pharmaceutical composition and any one of AZT, ddC, ddA, ddG, ddI, ddT, 3TC and d4T, or most preferred ddI, AZT, ddC or 3TC, in which such combinations are intended to be co-administered.

The pharmaceutical compositions can optionally contain a pharmaceutically acceptable carrier and/or excipient and/ or vehicle. A preferred method of the instant invention comprises preventing and/or inhibiting retrovital or HIV replication or eliminating HIV by treating a cell population, including cells infected with HIV, with an additive or synergistic combination of DANHSA or DTFANHSA and any one of AZT, ddC, ddA, ddG, ddI, ddT, 3TC and d4T, or most preferred ddI, AZT, ddC or 3TC, or by co-administering DANHSA or DTFANHSA as a pharmaceutical composition and any one of AZT, ddC, ddA, ddG, ddI, ddT, 3TC and d4T, or most preferred ddI, AZT, ddC or 3TC.

Additionally, a preferred method comprises treating an HIV-infected or AIDS patient with an additive or synergistic combination of DANHSA or DTFANHSA and any one of AZT, ddC, ddA, ddG, ddI, ddT, 3TC and d4T, or most preferred ddI, AZT, ddC or 3TC so as to prevent and/or inhibit HIV replication and/or eliminate HIV in the patient, or treating an HIV-infected or AIDS patient by co-administering DANHSA or DTFANHSA as a pharmaceutical composition and any one of AZT, ddC, ddA, ddG, ddI, ddT, 3TC and d4T, or most preferred ddI, AZT, ddC or 3TC so as to prevent and/or inhibit HIV replication and/or eliminate HIV in the patient.

DETAILED DESCRIPTION OF THE INVENTION

Figure 1:
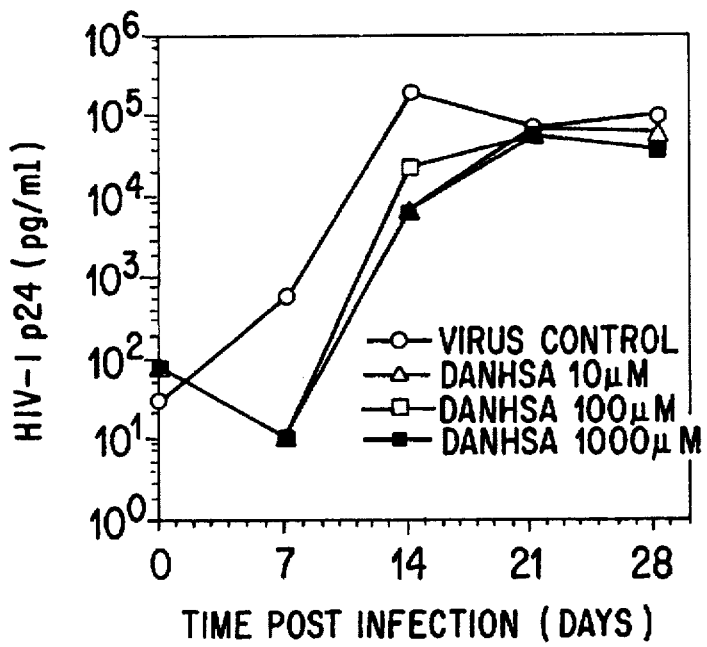
FIG. 1 graphically depicts a study of the antiviral activity of DANHSA on non-activated human PBMC infected with the HIV virus.

The present invention provides a new family of compounds which are useful as anti-inflammatory agents and broncho-dilating agents. The compounds are useful in a range of diseases which include arthritis and asthma. Additionally, these compounds are useful for anti-viral activity. This new family of compounds has the following formulas:

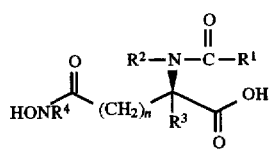

I (linear form)

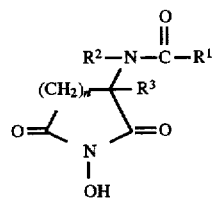

II (cyclic form)

wherein $R^1$ is an alkyl group of from 1 to 4 carbon atoms each optionally mono-, di-, or tri-substituted with halogen; each of $R^2$, $R^3$, $R^4$ is hydrogen or a straight or branched alkyl radical containing 1 to 8 carbon atoms, an alkenyl radical containing 2 to 8 carbon atoms, an alkynyl radical containing 2 to 8 carbon atoms, a cycloalkyl radical containing 3 to 6 carbon atoms, a cycloalkenyl radical containing from 4 to 6 carbon atoms or a bicycloalkyl radical containing 7 to 11 carbon atoms, these radicals optionally being substituted by at least one substituent selected from halogen, hydroxyl, alkyloxy containing 1 to 4 carbon atoms, dialkyl amino, in which each alkyl contains 1 to 4 carbon atoms, phenyl alkyl in which the alkyl contains 1 to 4 carbon atoms, cyclo alkyl containing 3 to 6 carbon atoms, optionally substituted phenyl, cyano, carboxyl, or alkyloxy carbonyl in which the alkyl contains 1 to 4 carbon atoms; and n is an integer from 0 to 6.

Compounds wherein $R^1$ is an alkyl group of from 1 to 4 carbons each optionally mono-, di-, or tri-substituted with halogen; $R^2$, $R^3$, and $R^4$ are each hydrogen and n=1 to 4 are more preferred. Compounds wherein $R^1$ is $CH_3$ or $CF_3$; $R^2$, $R^3$, and $R^4$ are each hydrogen and n=1 are most preferred.

The present invention further provides for compositions comprising these compounds including pharmaceutical compositions which optionally contain a pharmaceutically acceptable carrier, excipient, vehicle or combination thereof.

One general synthesis of these compounds is as follows:

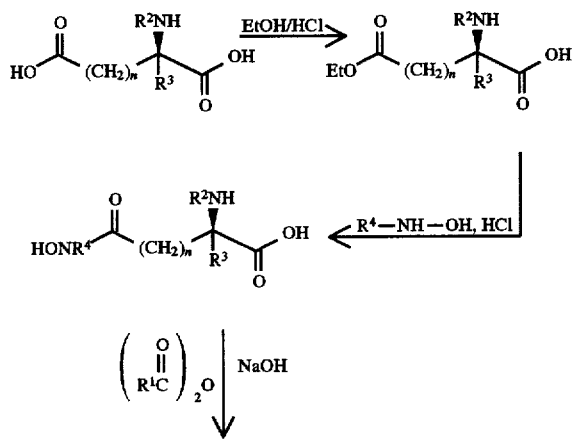

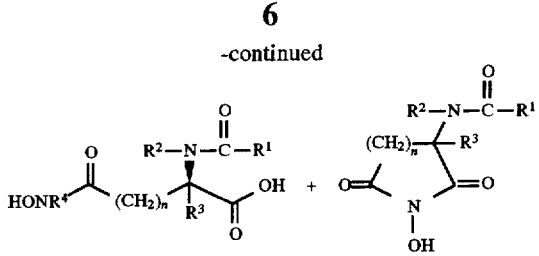

I (linear form)   II (cyclic form)

If n=0, the initial substrate of the reaction is D-serine.

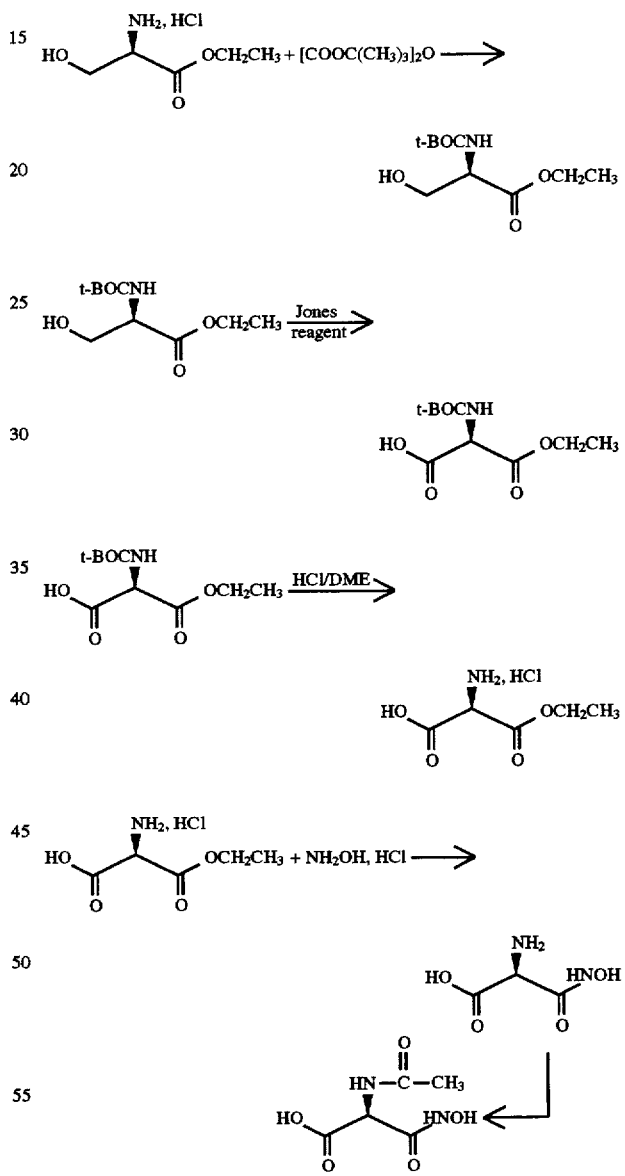

Further information regarding the synthesis is provided by Greenstein, J. P., Winitz, M., *Chemistry of the Amino Acids*, John Wiley, New York, 1961, pp. 927 and pp. 2065 and D. Stanley Tarbell, Yutaka Yamamoto, and Barry M. Pope, *Proc. Nat. Acad. Sci. USA*, Vol. 69, No 3, 1972, pp. 730–732, *Merck Index* 10, 8741, 8744, 8745, (1983), Warren, Briggs, Ber, 64, 29, (1931), M. Bodansky, A. Bodansky, *The Practice of Peptide Synthesis*, 125, (1984) and A. I. Vogel,

*Text-Book of Practical Organic Chemistry*, 371, 375–377 and 840, (3rd. edition, 1957). All of these references are incorporated herein, in their entirety, by reference.

Specifically, for example, D-acetamido-N-hydroxy succinamic acid and D-acetamido-N-hydroxy succinimide are obtained from D-aspartic acid or from D-asparagine according to the following sequence of reactions:

A. SYNTHESIS AND CHARACTERIZATION OF D-ACETAMIDO-N-HYDROXY SUCCINAMIC ACID (DANHSA) AND D-ACETAMIDO-N-HYDROXY SUCCINIMIDE chloride. The reaction mixture is stirred for about 2 hr. The solution is diluted by addition of 250 ml of absolute ethanol. Triethylamine is then added dropwise until the solution becomes alkaline. After standing for 16 hr at +4° C., the obtained crystals are filtered, washed successively with cold absolute ethanol and ether, then dried. The reaction yields 11.5 g of D-aspartic acid β-ethyl ester (71%).

NMR$^{13}$C in D$_2$O (75.47 MHz): d 14.3 ppm ($\underline{C}$H$_3$) 35.04 ppm ($\underline{C}$H$_2$); 50.2 ppm ($\underline{C}$H); 63.7 ($\underline{C}$H$_2$—O); 171.7 ppm ($\underline{C}$=O ester); 172.2 ppm ($\underline{C}$=O-acid).

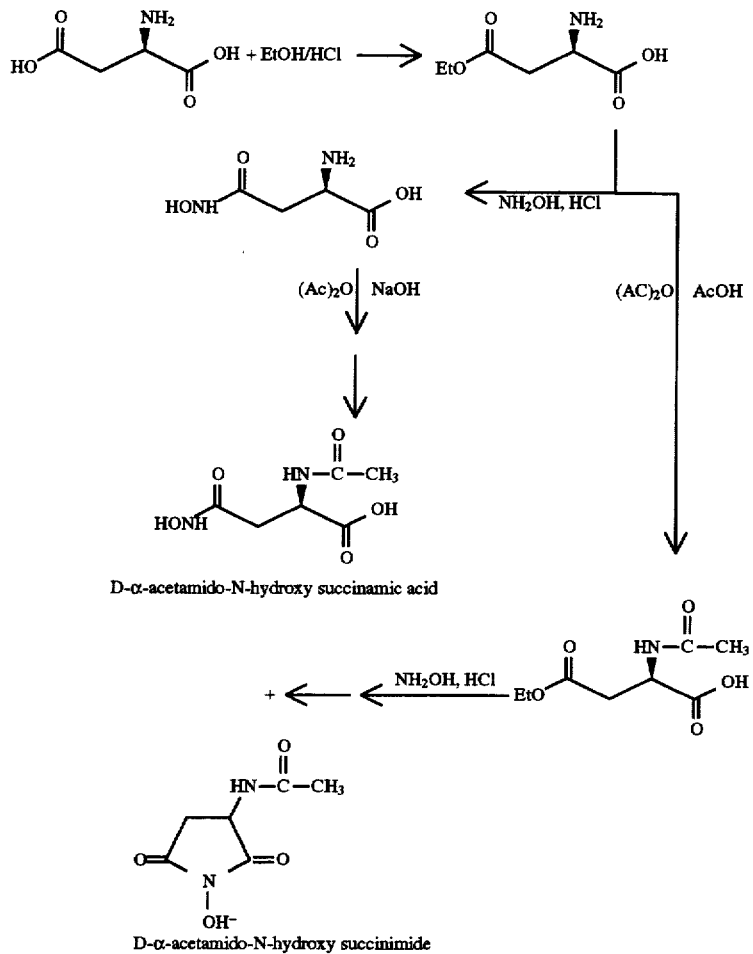

STEP 1:
SYNTHESIS OF D-ASPARTIC ACID β-ETHYL ESTER

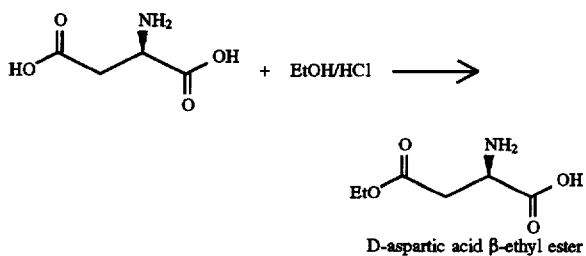

D-aspartic acid β-ethyl ester 13.31 g of D-aspartic acid (0.1 mole) are dissolved in 135 ml of absolute ethanol containing 8.7 g of dry hydrogen

STEP 2:
SYNTHESIS OF D-ASPARTIC ACID β-HYDROXAMATE

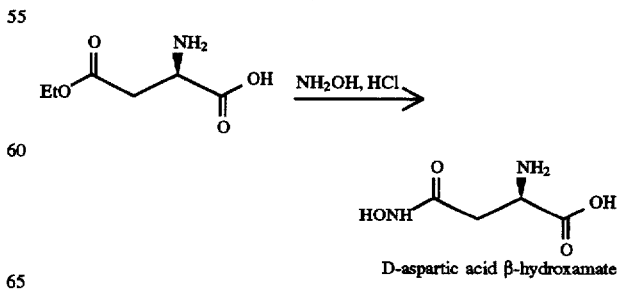

D-aspartic acid β-hydroxamate 0.1 mole of D-aspartic acid β-ethyl ester is dissolved in 200 ml of methanol, 0.2 mole of hydroxylamine hydrochloride is then added and the mixture is stirred until complete dissolution occurs. 0.4 mole of triethylamine is added and stirring is continued at room temperature for about 48 hr. The precipitate formed is collected on a filter. This crude product is recrystallized by dissolution in water, then diluted in absolute ethanol. This solution is kept at +4° C. for 12 hr. The crystals are filtered, washed with absolute ethanol and air-dried. This reaction yields 50 to 70% of D-Aspartic acid β-Hydroxamate.

Elemental analyses: Calculated for $C_4H_8N_2O_4$ (148.1): C=32.41; H=5.40; N=18.90; O=43.21. Found: C=32.38; H=5.31; N=18.89; O=43.26.

RMN $^1H$ in $D_2O$ (300.13 MHz): (d) 2.7 ppm (dd, 1H, j=7.5, 16 Hz); 2.8 ppm (dd, 1H, j=4.5, 16 Hz); 4 ppm (dd, 1H, j=4.5, 7.5 Hz); 4.8 ppm (s, HOD).

NMR$^{13}$C in $D_2O$ (75.47 MHz): d 32.8 ppm ($\underline{C}H_2$); 51.7 ppm ($\underline{C}H$); 169.0 ppm ($\underline{C}$=O hydroxamate); 173.4 ppm ($\underline{C}$=O-acid).

STEP 3:

SYNTHESIS OF D-ACETAMIDO-N-HYDROXY SUCCINAMIC ACID AND D-ACETAMIDO-N-HYDROXY SUCCINIMIDE

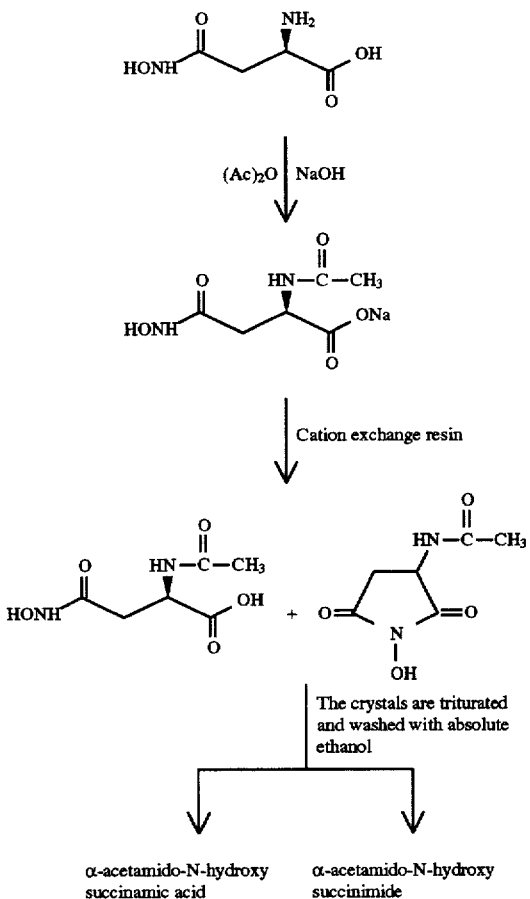

29.6 g of D-Aspartic acid β-Hydroxamate are dissolved in 200 ml of cold 1N NaOH. The solution is stirred in an ice-water bath. 40 ml of 1N NaOH are added followed by 4.08 g of acetic anhydride. At this stage the pH of the solution should be alkaline; if not a small volume of 1N NaOH should be added to obtain an alkaline pH. This process (addition of NaOH and acetic anhydride) is repeated four more times. At each step, the pH of the solution should be evaluated for adjustment as previously described. Stirring of solution is maintained at room temperature for 16 hr–18 hr. The reaction mixture is then applied to a cation exchange resin Dowex 50 W×8 column. The elution is performed with water and the effluent obtained is evaporated in vacuo to dryness. The separation of the linear form (α-acetamido-N-hydroxy-succinamic acid) from the cyclic form (α-acetamido-N-hydroxy-succinimide) is achieved by triturating the crystals, washing with absolute ethanol, filtering and drying. This reaction yields 22 to 25 g of DANHSA.

EVIDENCE OF CHEMICAL STRUCTURE

For D-Acetamido-N-Hydroxy Succinimide Acid:

Elemental analyses: Calculated for $C_6H_{10}N_2O_5$ (190.1): C=37.87; H=5.26; N=14.72; O=42.08. Found: C=37.84; K=5.19; N=14.5; O=42.25

Nuclear Magnetic resonance (NMR):

NMR spectra were recorded on a Bruker AM spectrometer in $D_2O$ or DMSO-$D_6$ at 300.13 MHz and 75.47 MHz with tetramethylsilane (TMS) as external standard. Chemical shifts (d) are reported in ppm (parts per million) relative to TMS.

RMN $^1H$ in $D_2O$ (300.13 MHz): (d) 1.8 ppm (s 3H); 2.6 ppm (dd, 1H, j=7.5, 15 Hz); 2.7 ppm (dd, 1H, j=5.5, 15 Hz); 4.7 ppm (dd, 1H, j=5.5, 7.5 Hz); 4.8 ppm (s, HOD).

RMN $^1H$ in DMSO-D6 (300.13 MHz): d 12.6 ppm (s, 1H acid); 10.4 ppm (s, 1H N$\underline{H}$); 8.8 ppm (s, 1H NO$\underline{H}$); 8.1 ppm (d,1H N$\underline{H}$). 4.5 ppm (dd, 1H C$\underline{H}$), 2.4 et 2.3 ppm (2 dd, 2H C$\underline{H}_2$); 1.8 ppm (s, 3H C$\underline{H}_3$).

NMR$^{13}$C in $D_2O$+1 drop NaOD (75.47 MHz): d 22.5 ppm ($\underline{C}H_3$); 36.1 ppm ($\underline{C}H_2$); 53.05 ppm ($\underline{C}H$); 164.7 ppm ($\underline{C}$=O acetyl); 174.1 ppm ($\underline{C}$=O hydroxamate); 178.6 ppm ($\underline{C}$=O-acid).

For D-Acetamido-N-Hydroxy Succinimide:

Elemental analyses: Calculated for $C_6H_8N_2O_4$ (172.1): C=41.83; H=4.65; N=16.27; O=37.20. Found: C=41.55; H=4.75; N=16.55; O=37.42.

NMR$^{13}$C in $D_2O$ (75.47 MHz): δ21.9 ppm ($\underline{C}H_3$); 33.2 ppm ($\underline{C}H_2$); 47.3 ppm ($\underline{C}H$); 174.5 ppm ($\underline{C}$=O acetyl); 173.9 and 175 ppm ($\underline{C}$=O).

RMN $^1H$ in DMSO-D6 (300.13 MHz): δ 10.7 ppm (s, 1H NO$\underline{H}$); 8.5 ppm (d, 1H N$\underline{H}$). 4.3 ppm (d d, 1H C$\underline{H}$), 2.9 et 2.4 ppm (2 d d, 2H C$\underline{H}_2$); 1.8 ppm (s 3H C$\underline{H}_3$)

The colorimetric determination of hydroxamic function:

The hydroxamic function of DANHSA was observed by complex with the ferric ion, on a Beckman DU-70 spectrophotometer. The iron complexes of hydroxamic acid are typically red—violet showing maximal absorption in the following wave range: 500–550 nm.

Thin-layer Chromatography (TLC):

TLC was performed on Merck Kieselgel 60 $F_{254}$ (0.2 mm layer thickness) in ethanol—water 8:2 (v/v) DANHSA gave a single spot, which was visualized by spraying with aqueous 2% Ferric chloride.

B. SYNTHESIS AND CHARACTERIZATION OF D-TRIFLUOROACETAMIDO-N-HYDROXY SUCCINAMIC ACID (DTFANHSA) AND D-TRIFLUOROACETAMIDO-N-HYDROXY SUCCINIMIDE

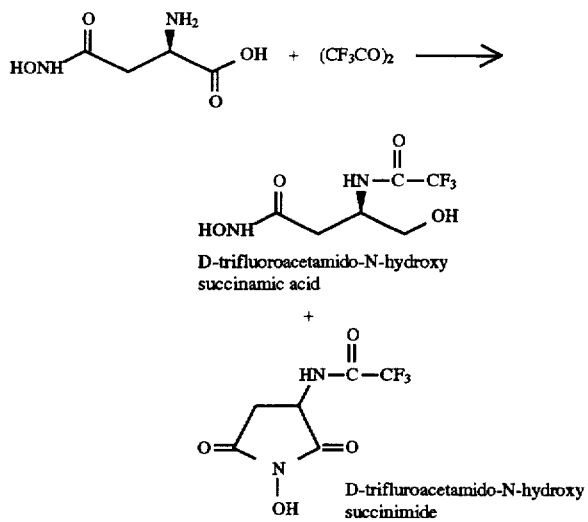

0.1 mole of D-aspartic acid β-hydroxamate is dissolved in 60 ml of anhydrous trifluoroacetic acid. 0.14 mole of trifluoroacetic anhydride is added dropwise over a period of 1½ to 2 hr. with stirring. After 4 hr, the excess of anhydride and trifluoroacetic acid is distilled under reduced pressure at 30°–40° C. The residue is dissolved in water and filtered to cation exchange resin Dowex 50 W×8 column. The elution is performed with water and the effluent obtained is evaporated in vacuo to dryness. The separation of the linear form (α-trifluoro-acetamido-N-hydroxy succinamic acid) from the cyclic form (α-trifluoroacetamido-N-hydroxy succinimide) is achieved by triturating the crystals, recrystallizing with ether, filtering and drying. This reaction yields 60% of DTFANHSA.

Elemental analyses: Calculated for $C_6H_7N_2O_5F_3$, ½ $H_2O$ (253.1): C=28.44; H=3.16; N=11.06; F=23.35. Found: C=28.38; H=3.18; N=10.68; F=22.45.

Nuclear Magnetic resonance (NMR):

$NMR^{13}C$ in $D_2O$ (75.47 MHz): d 32.4 ppm ($\underline{C}H_2$); 46.8 ppm ($\underline{C}H$);. 121.5; 117.7; 113.9 and 110.2 ppm (q, $\underline{C}F_3$ j=3.5 ppm) 160.3; 159.8; 159.3 and 158.8 ppm (q, $\underline{C}$=O j=0.5 ppm TFA); 172.7 ppm ($\underline{C}$=O hydroxamate); 173.1 ppm ($\underline{C}$=O-acid).

This new family of compounds either alone or in combination with at least one reverse transcriptase (RT) inhibitor, is useful for preventing, inhibiting or eliminating the spread of viruses and, in particular, for the treatment of a cell population in the presence of a retrovirus. Additionally, the invention encompasses pharmaceutical compositions intended, in particular, for the treatment and prevention of retroviral infections, especially those linked to HIV and AIDS wherein the compositions contain an additive or synergistic combination of at least any one of the new family of compounds including D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof and at least one reverse transcriptase inhibitor; in particular an additive or synergistic combination of a dideoxynucleoside or more than one dideoxynucleoside and DANHSA or DTFANHSA; most preferably an additive or synergistic combination of any one of AZT, ddC, ddI or 3TC and DANHSA or DTFANHSA as active principle, in a pharmaceutically acceptable vehicle, or co-administered. The compositions of the present invention can also contain inert or pharmacodynamically active additives, carriers and/or excipients.

The pharmaceutical compositions of the invention can take the form of a lyophilized powder of the active substance, to be dissolved immediately before use in a physiological solution for the purpose of injection. The medicament can then be administered parenterally, for example intravenously, intraperitoneally, in the cerebrospinal fluid, and the like. For injection, the active principle is dissolved in a physiological solution until the desired concentration for administration is obtained.

The pharmaceutical compositions according to the invention can also take a form which is suitable for oral administration. For example, suitable forms are tablets, hard gelatin capsules, dragées, powders and granules. The formation of such oral forms is well-known to those skilled in the art. Any of the known formulations are useful in preparing the instant oral pharmaceutical compositions.

As regards the dosage of the medicament according to the invention, it will be clear to the artisan that the doses to be administered are variable according to the treatment period, and frequency of administration, the host and the nature and severity of the disease.

The compositions of the present invention are administered in substantially non-toxic dosage concentrations sufficient to insure the release of a sufficient dosage unit of at least one compound of the new family of compounds herein disclosed for those compositions comprising same, into the patient to provide the desired inhibition of the spread of the retrovirus. For the compositions comprising a synergistic combination, these are also administered in substantially non-toxic dosage concentrations sufficient to insure the release of a sufficient dosage unit of the synergistic combination into the patient to provide the desired inhibition of the spread of the retrovirus.

The actual dosage administered will be determined by physical and physiological factors such as age, body weight, severity of condition, and/or clinical history of the patient. With these considerations in mind, the dosage of the compositions comprising the compounds of the present invention and those comprising an additive or synergistic combination for a particular subject can be readily determined by the physician. It might be noted that in extreme cases a dosage approaching the toxic level may be the acceptable treatment protocol.

Compositions of the present invention comprising any one of the herein disclosed new family of compounds, such as for example, DANHSA or DTFANHSA, may contain these compounds in a concentration range of from about 0.5 µM to about 20,000 µM; preferably from about 1 µM to about 10,000 µM; more preferably from about 5 µM to about 5,000 µM; and most preferably from about 10 µM to about 1,000 µM.

Other compositions may contain these compounds, having the same ranges, in combination with at least one inhibitor of reverse transcriptase or at least one dideoxynucleoside such as, for example ddI, at concentrations which are generally known and used in the art, or preferably from about 0.01 µM to about 200 µM; more preferably from about 0.1 µM to about 100 µM; most preferably from about 0.2 µM to about 10 µM.

For example, in the treatment of HIV-infected and AIDS patients, compositions can be administered in dosage ranges such as to provide plasma concentrations in the range of from about 0.5 μM to about 20,000 μM; preferably from about 1 μM to about 10,000 μM; more preferably from about 5 μM to about 5,000 μM; and most preferably from about 10 μM to about 1,000 μM for the compounds of the present invention and for the reverse transcriptase inhibitor, a range which is generally known and used in the art, or preferably from about 0.01 μM to about 200 μM; more preferably from about 0.1 μM to about 100 μM; most preferably from about 0.2 μM to about 10 μM.

The present invention also covers the use of an RT inhibitor and any one of the new family of compounds including D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof in combination with other medicinal compositions intended for the treatment of retroviral infections. Immunostimulants and immunomodulators such as for example cytokines, including IL-2, IL-12 and interferon molecules can be used in combination with the present invention.

A preferred range for in vitro administration of the compositions of the present invention is from about 0.5 μM to about 20,000 μM; preferably from about 1 μM to about 10,000 μM; more preferably from about 5 μM to about 5,000 μM; and most preferably from about 10 μM to about 1,000 μM for the compounds of the present invention. For the reverse transcriptase inhibitor, a preferred range for in vitro administration is the range which is generally known and used in the art, or preferably from about 0.01 μM to about 200 μM; more preferably from about 0.1 μM to about 100 μM; and most preferably from about 0.2 μM to about 10 μM.

EXAMPLES

The following examples of specific embodiments of the present invention are offered for illustrative purposes only and are not limiting with respect to the scope of the disclosure or claim coverage.

Testing of the mixture of DANHSA or DTFANHSA and any one of ddI, AZT, ddC or 3TC on the production of HIV was conducted on human peripheral blood mononuclear cells (PBMC) infected with HIV without prior activation/ proliferation of these cells by phytohemagglutinin (PHA) and interleukin-2 (IL-2).

TABLE 1 is a study of the anti-viral activity of DANHSA, AZT, ddC, ddI and 3TC alone and of DANHSA in combination with AZT, ddC, ddI and 3TC in non-activated human peripheral blood mononuclear cells (PBMC) infected with HIV as measured by p24 gag protein expressed in pg/ml.

TABLE 2 is a study of the anti-viral activity of DTFANHSA, AZT, ddC, ddI and 3TC alone and of DTFANHSA in combination with AZT, ddC, ddI and 3TC in non-activated human peripheral blood mononuclear cells (PBMC) infected with HIV as measured by p24 gag protein expressed in pg/ml.

Example 1

The anti-viral activity of DANHSA alone and in combination with RT inhibitors on non-activated resting human lymphocytes infected with HIV (see Table 1 and FIGS. 1 to 5).

PBMC were incubated with the viral strain HIV-1 Lai for two hours at 37° C. with a multiplicity of infection of $10^4$ $TCID_{50}$ per $10^6$ cells. Unbound virus was then eliminated by two successive washes with culture medium and the cells were seeded at a density of $10^6$ cells/ml in the presence of various drug concentrations. On day 7, supernatant were collected for p24 assay and cells were washed 3 times to remove traces of drug. Cells were then submitted to PHA activation by culture in fresh medium containing PHA (Murex 1 μg/ml) and recombinant IL-2 (Roussel 10 U/ml). After 48 hrs of incubation, cells were washed to remove PHA and resuspended in fresh medium containing IL-2. These cultures were maintained for 3 weeks (days 9 to 28): on days 14, 21 and 28, half of the medium was taken and replaced either by fresh medium containing IL-2 (days 21 and 28) or by PHA-activated PBL from blood of healthy donors in RPMI medium 1640 supplemented with IL-2 on day 14 ($4 \times 10^5$ cells/ml). Supernatant were kept for HIV p24 gag protein ELISA assay (DuPont).

Three concentrations of DANHSA were studied: 10, 100 and 1000 μM, and resulted in anti-HIV activity as measured by inhibition of viral production compared to infected non-treated control (see FIG. 1).

On day 7, 10 μM DANHSA resulted in 98% inhibition, 100 μM in 98.2% inhibition, and 1000 μM in 98.2% inhibition.

On day 14, 10 μM resulted in 96.5%, 100 μM in 88.2%, and 1000 μM in 96.7% inhibition respectively.

A lesser inhibition is observed on day 21, and persists through day 28 with 10 μM resulting in 34.6%, 100 μM in 60%, and 1000 μM in 60.8% inhibition respectively.

Figure 2A:
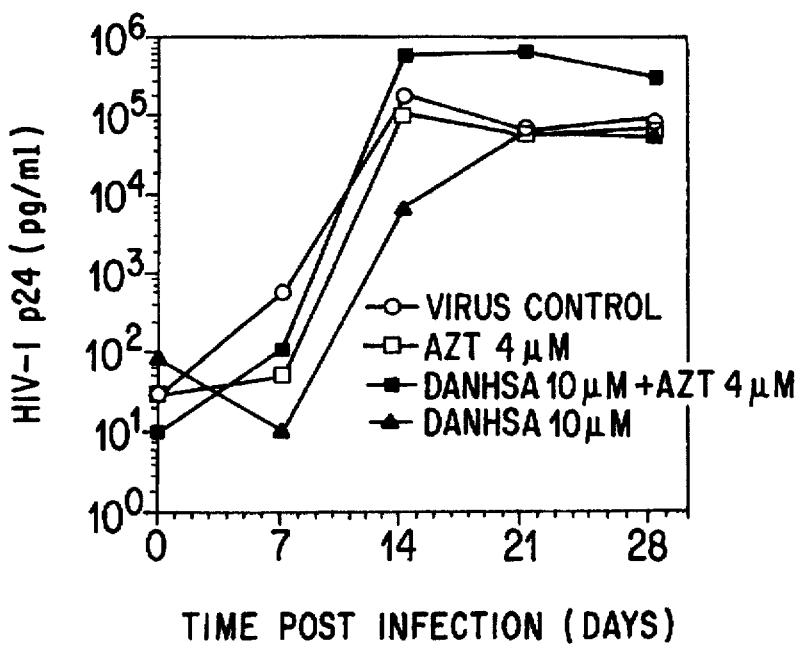
FIGS. 2(a, b, c) each graphically depicts a study of the antiviral activity of DANHSA in combination with AZT on non-activated human PBMC infected with the HIV virus.
Figure 2B:
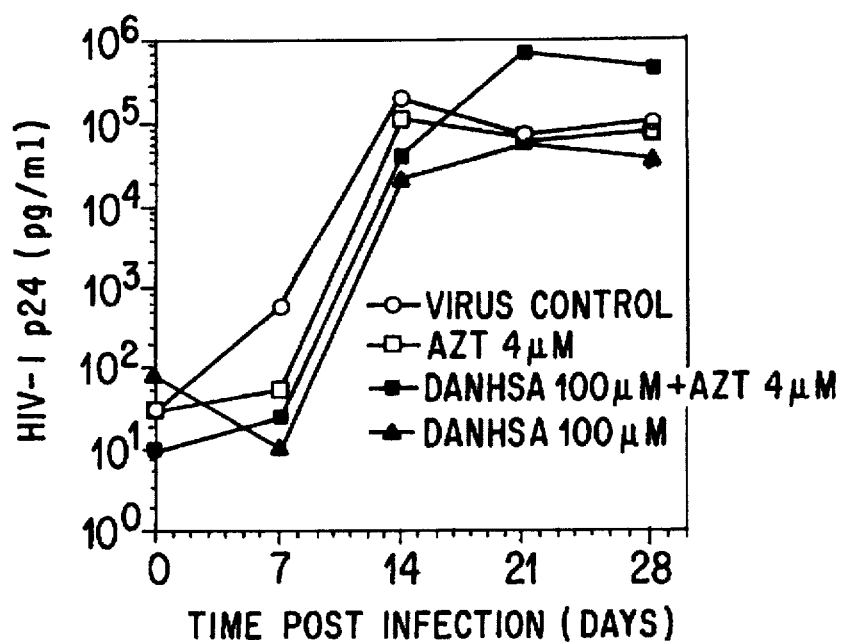
Figure 2C:
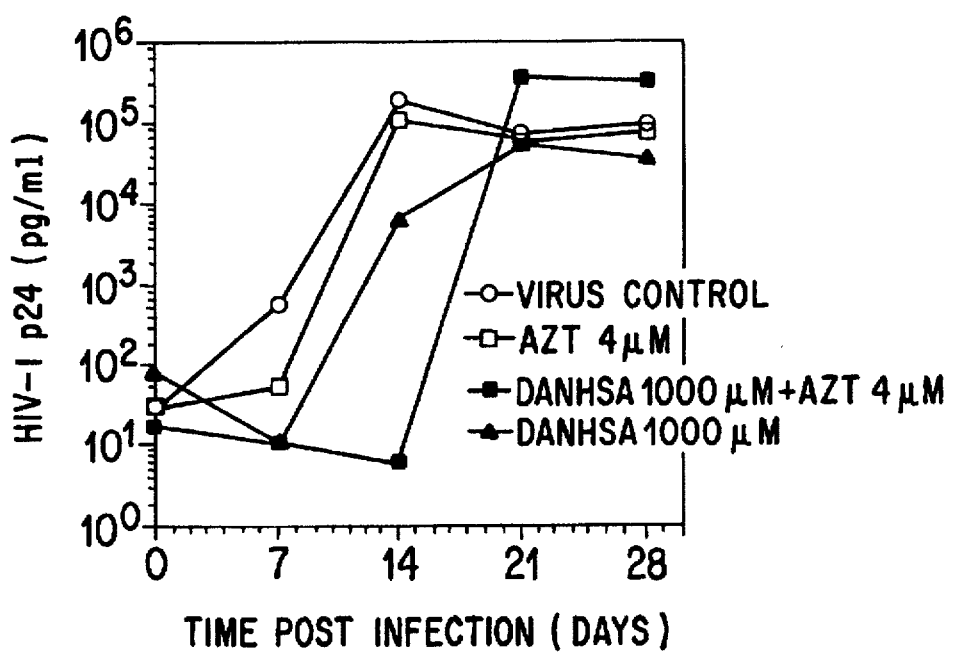
Figure 3A:
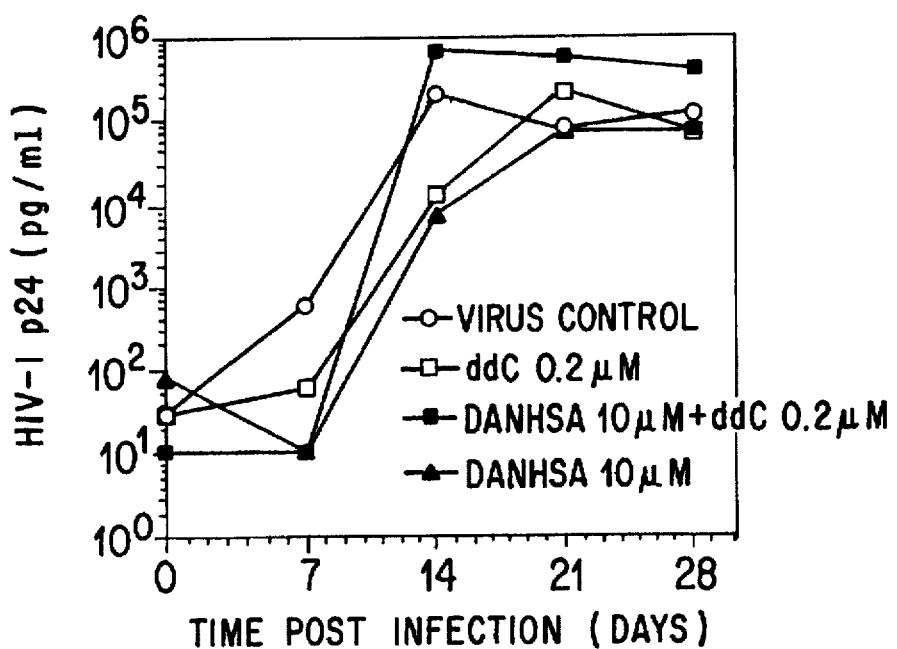
FIGS. 3(a, b, c) each graphically depicts a study of the antiviral activity of DANHSA in combination with ddC on non-activated human PBMC infected with the HIV virus.
Figure 3B:
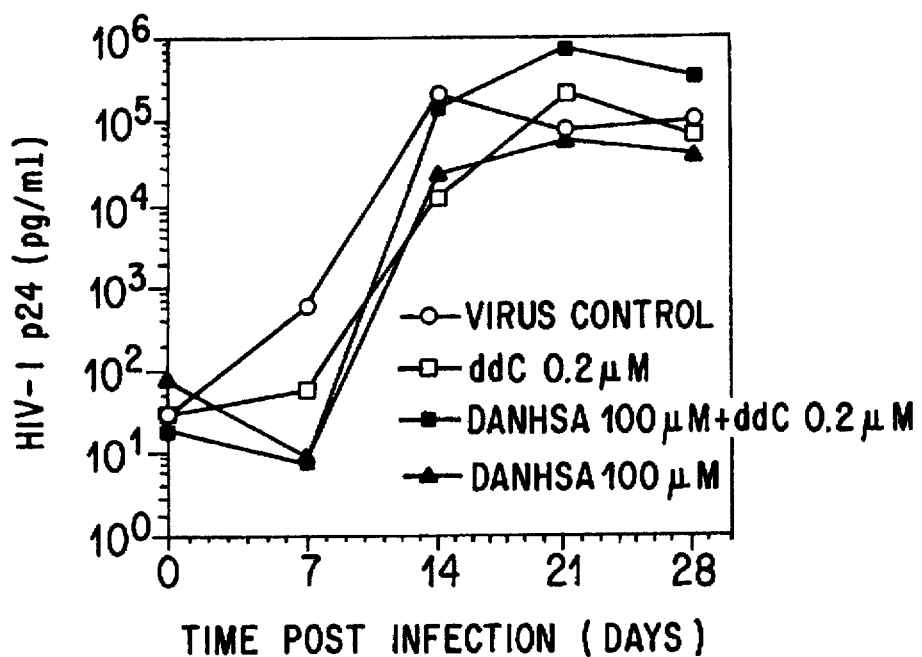
Figure 3C:
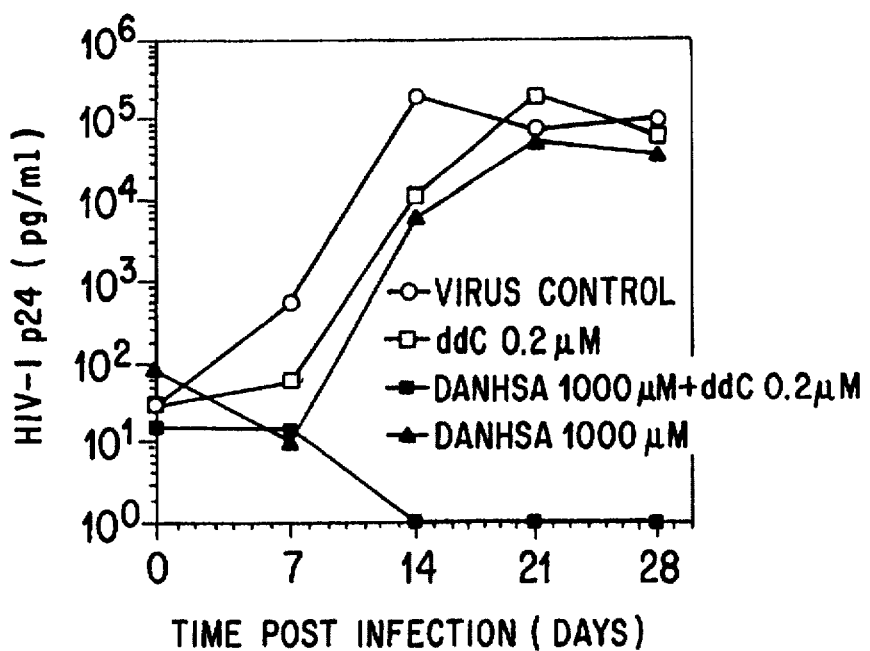
Figure 4A:
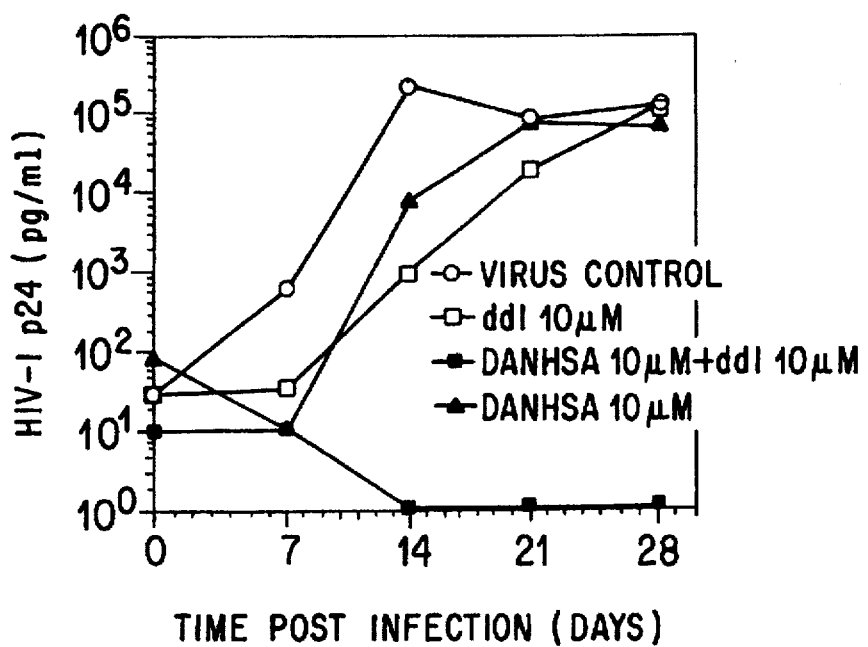
FIGS. 4(a, b, c) each graphically depicts a study of the antiviral activity of DANHSA in combination with ddI on non-activated human PBMC infected with the HIV virus.
Figure 4B:
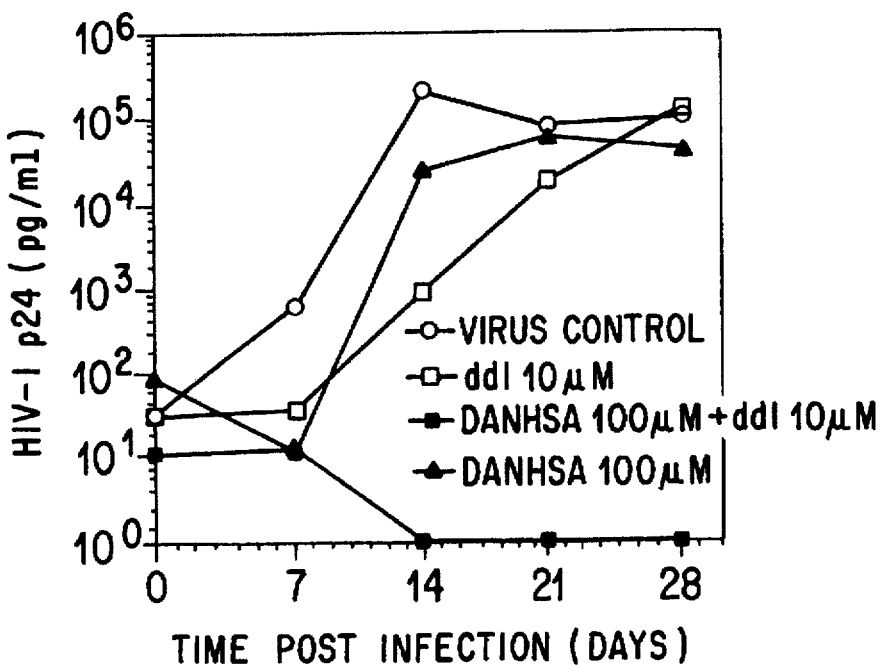
Figure 4C:
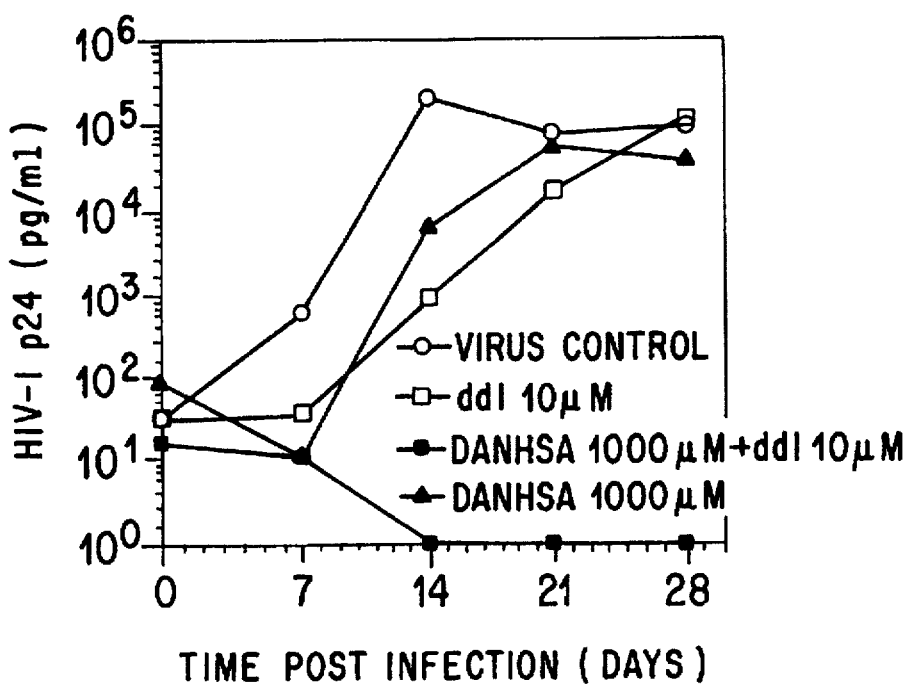
Figure 5A:
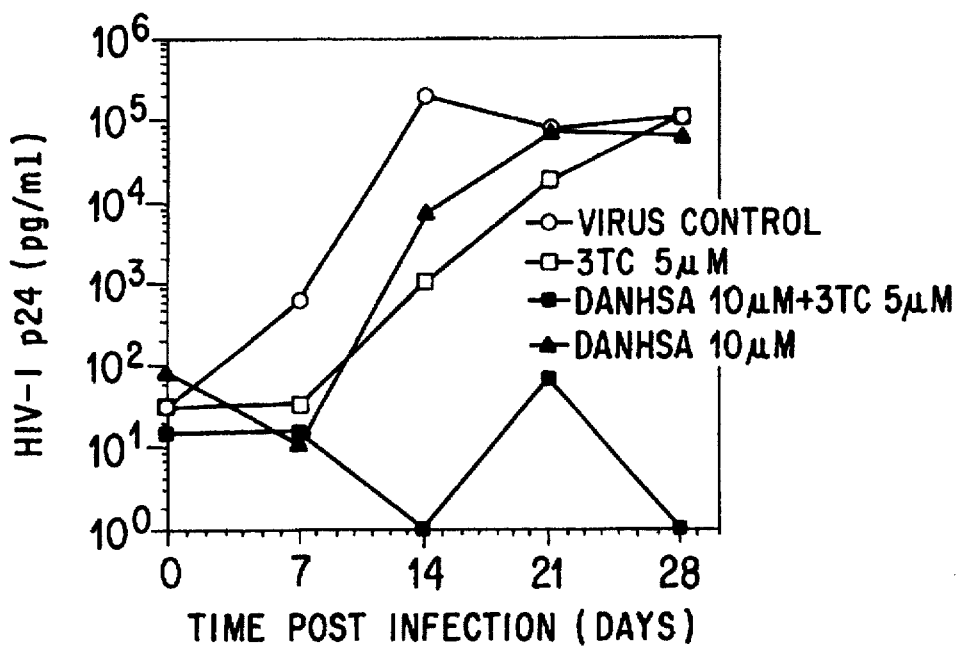
FIGS. 5(a, b, c) each graphically depicts a study of the antiviral activity of DANHSA in combination with 3TC on non-activated human PBMC infected with the HIV virus.
Figure 5B:
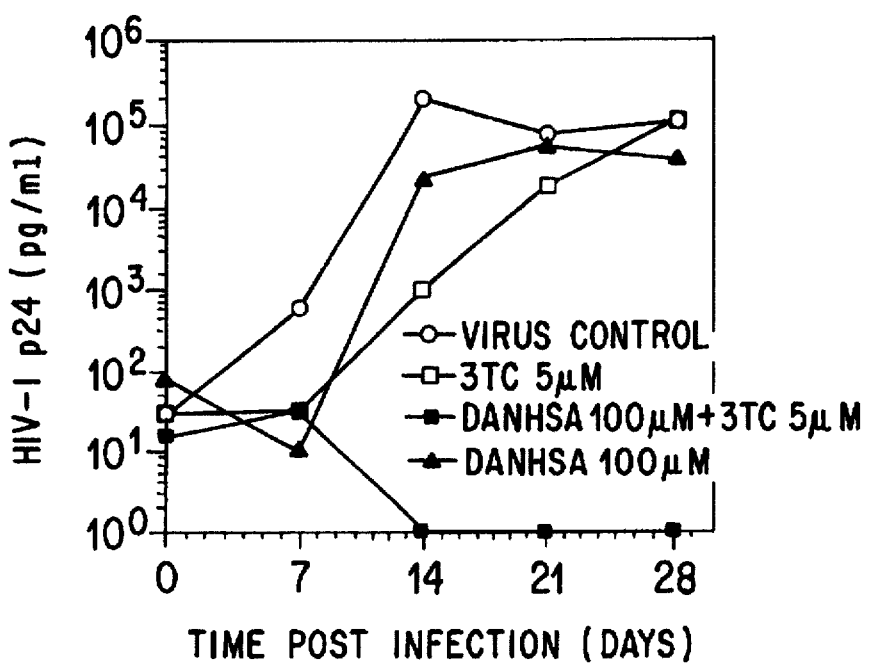
Figure 5C:
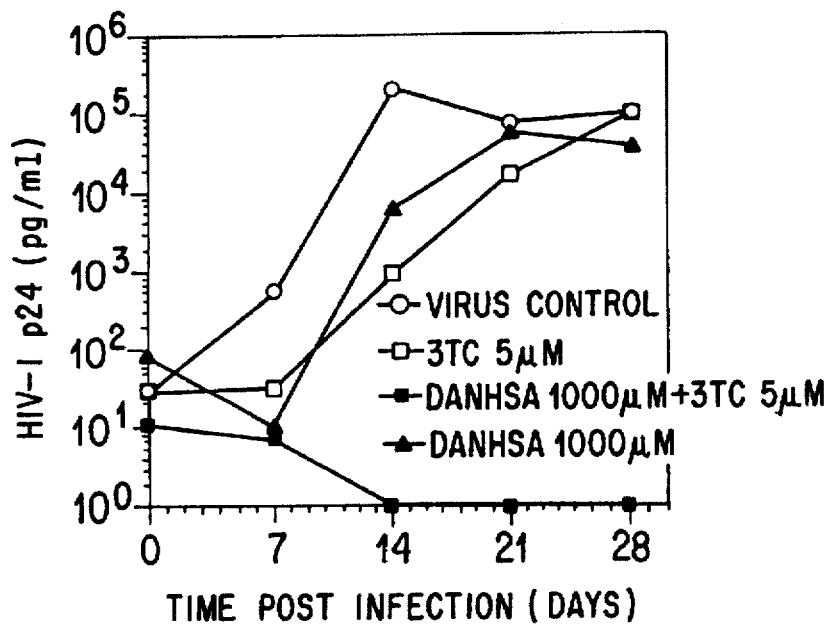
Figure 6:
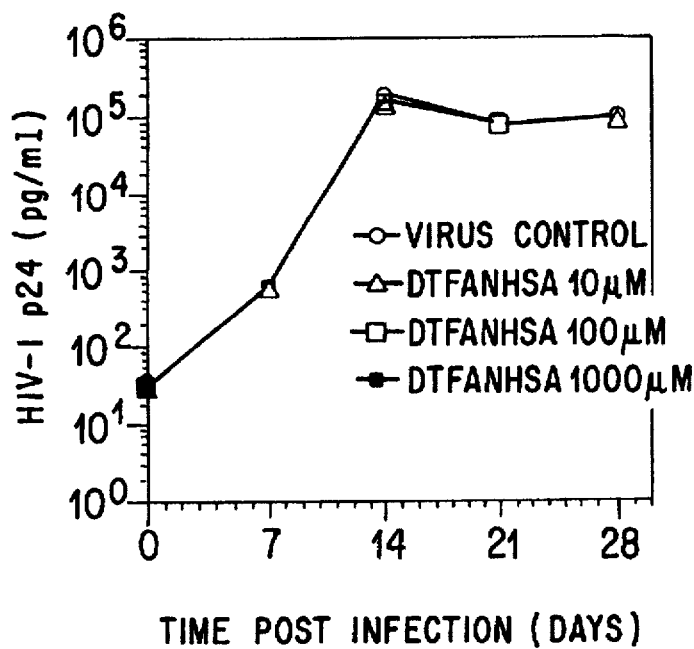
FIG. 6 graphically depicts a study of the antiviral activity of DTFANHSA on non-activated human PBMC infected with the HIV virus.
Figure 7A:
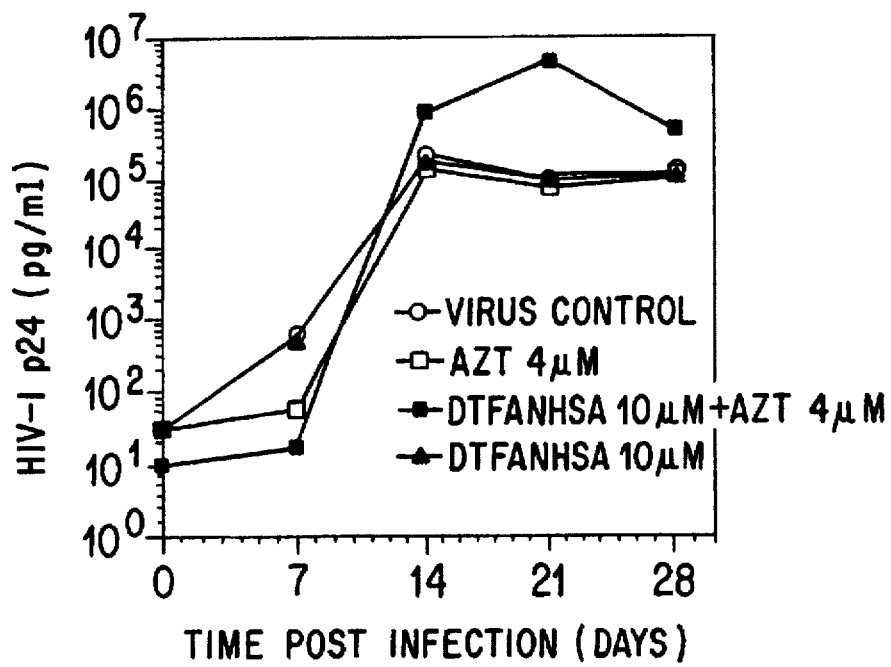
FIGS. 7(a, b, c) each graphically depicts a study of the antiviral activity of DTFANHSA in combination with AZT on non-activated human PBMC infected with the HIV virus.
Figure 7B:
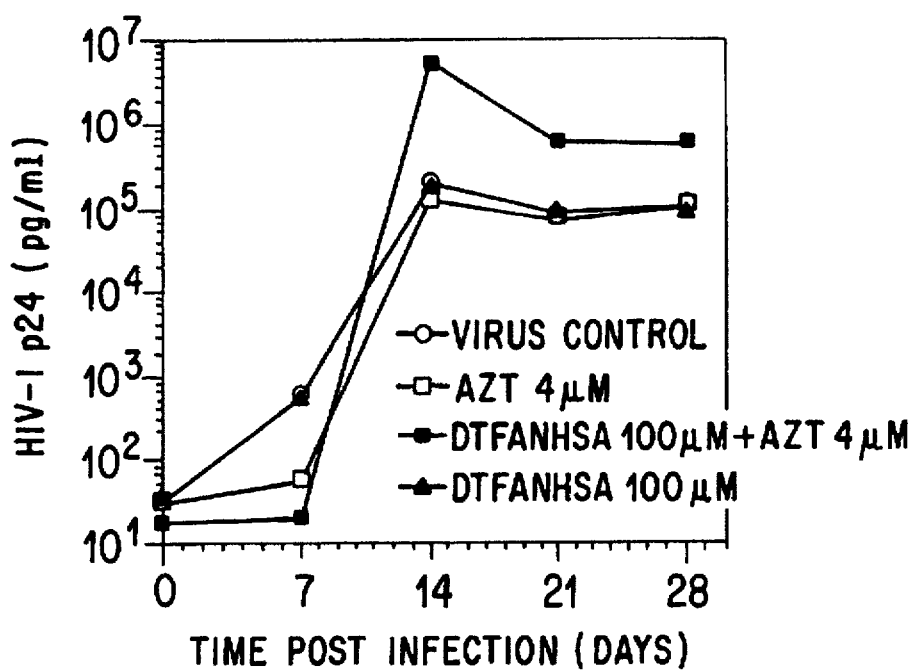
Figure 7C:
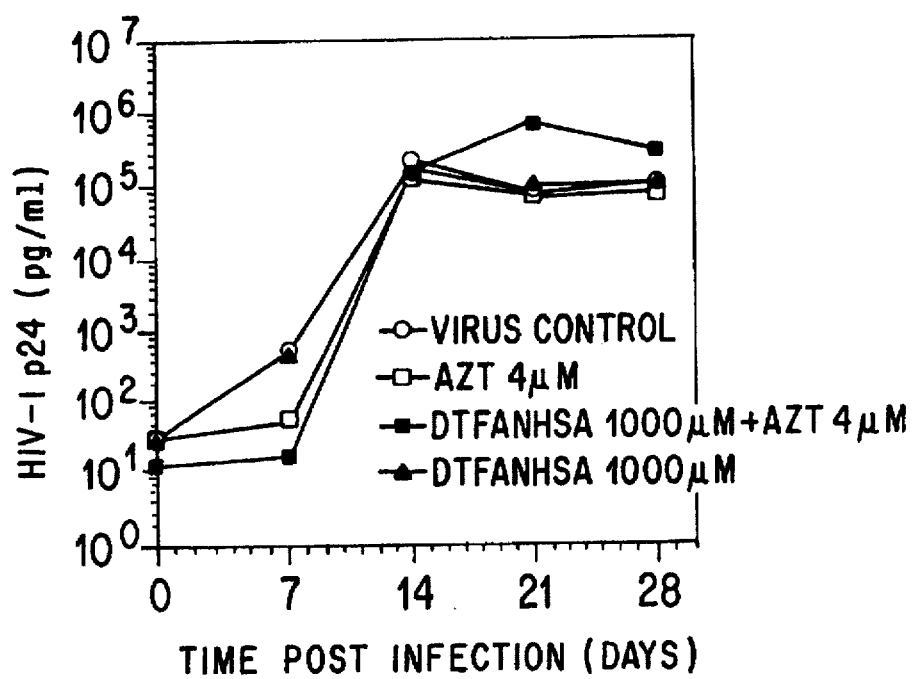
Figure 8A:
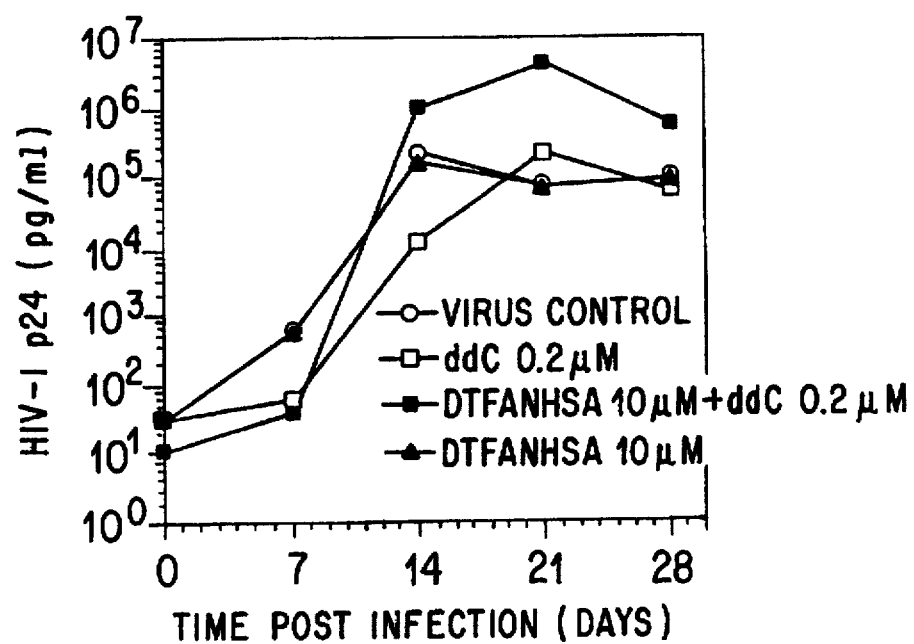
FIGS. 8(a, b, c) each graphically depicts a study of the antiviral activity of DTFANHSA in combination with ddC on non-activated human PBMC infected with the HIV virus.
Figure 8B:
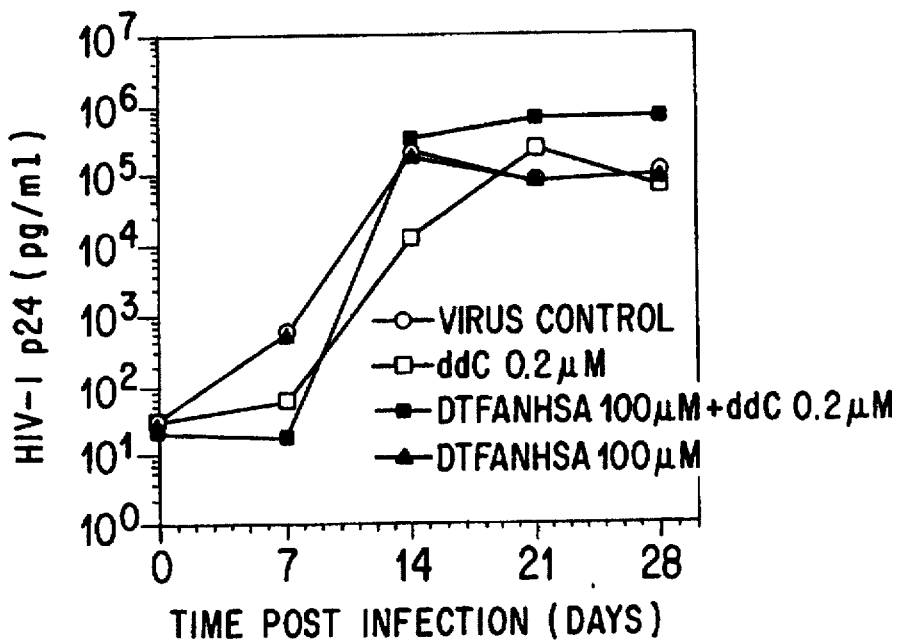
Figure 8C:
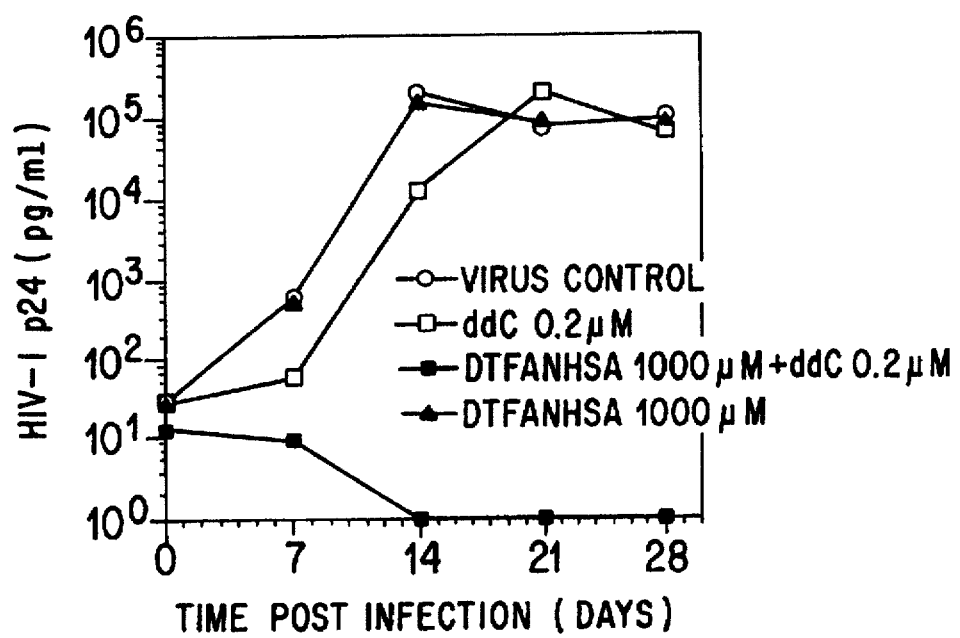
Figure 9A:
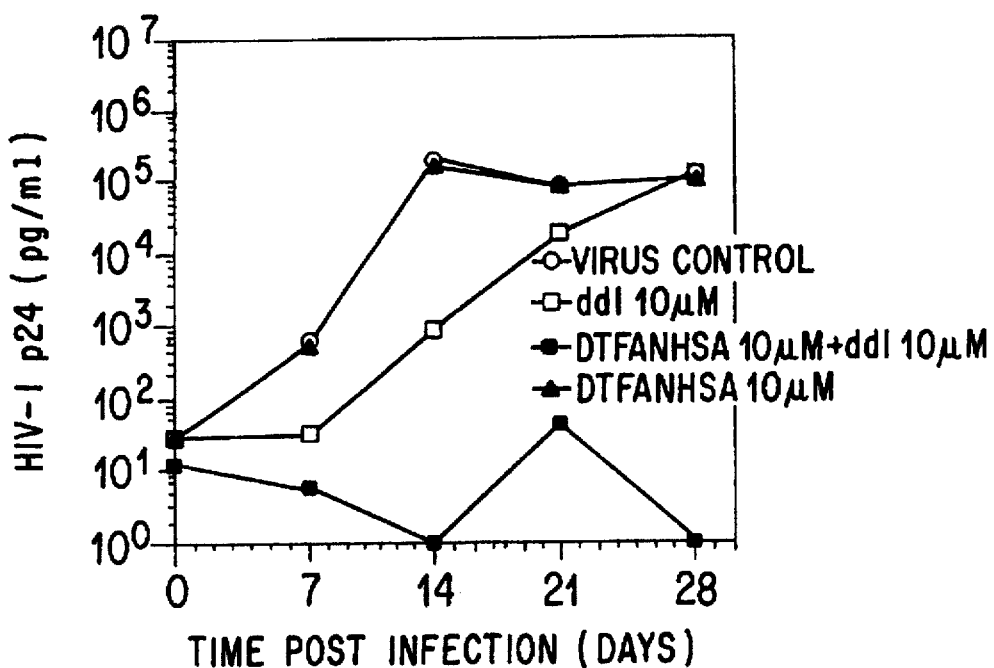
FIGS. 9(a, b, c) each graphically depicts a study of the antiviral activity of DTFANHSA in combination with ddI on non-activated human PBMC infected with the HIV virus.
Figure 9B:
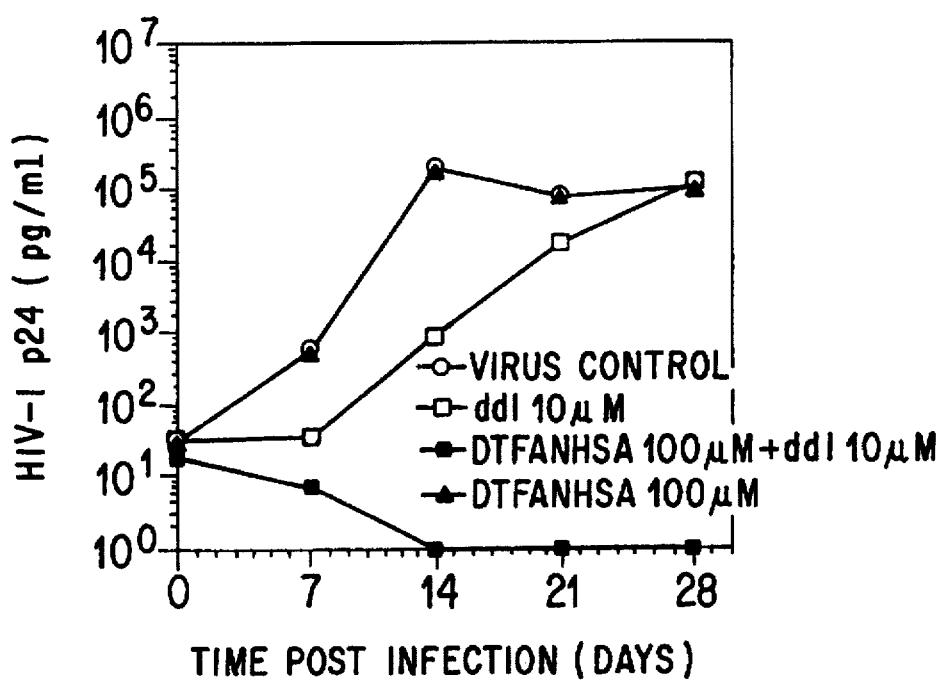
Figure 9C:
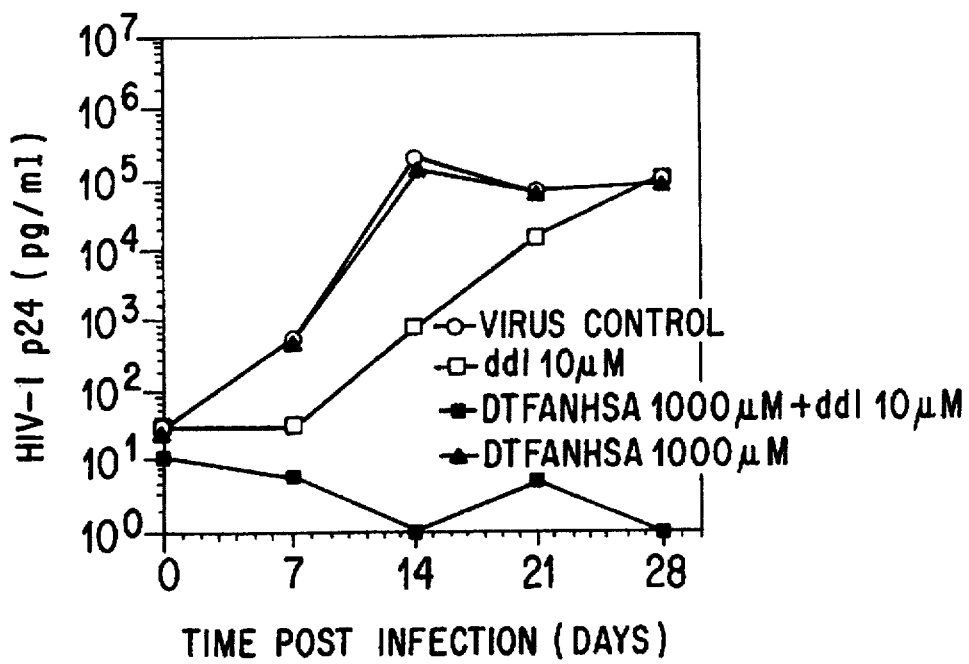
Figure 10A:
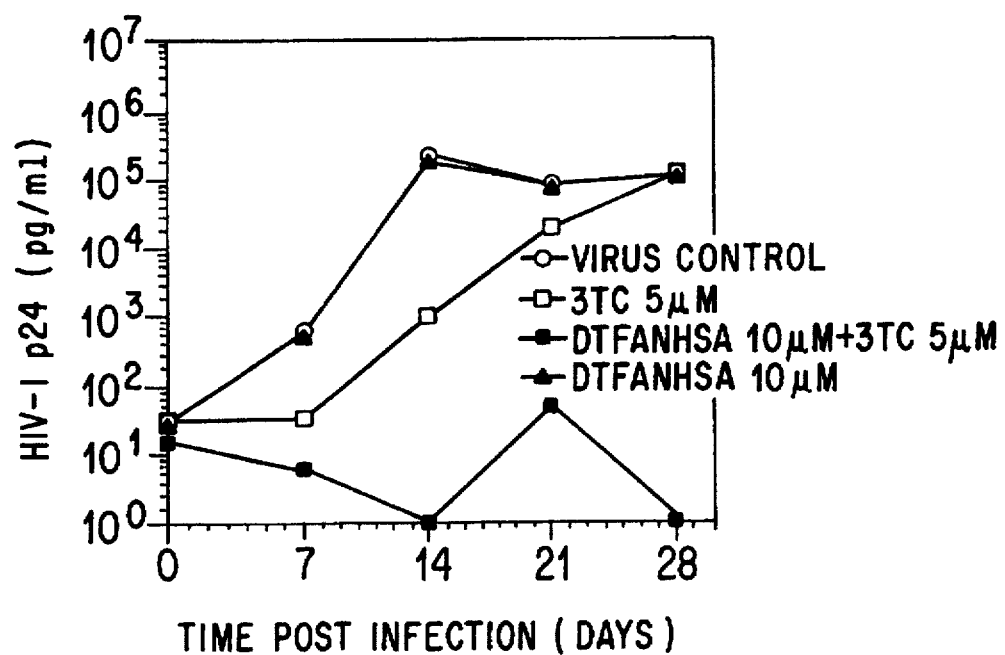
FIGS. 10(a, b, c) each graphically depicts a study of the antiviral activity of DTFANHSA in combination with 3TC on non-activated human PBMC infected with the HIV virus.
Figure 10B:
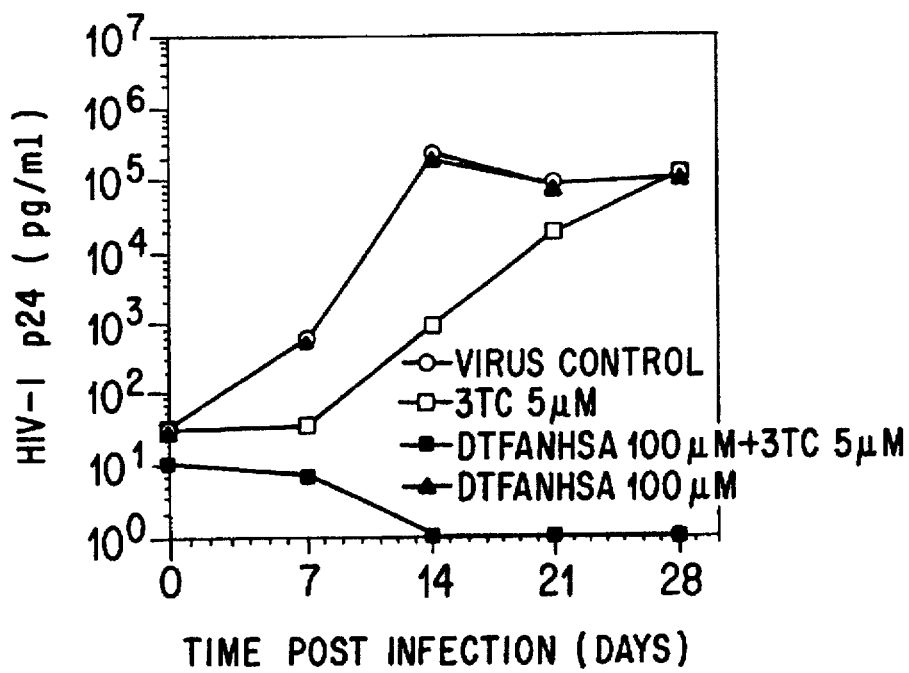
Figure 10C:
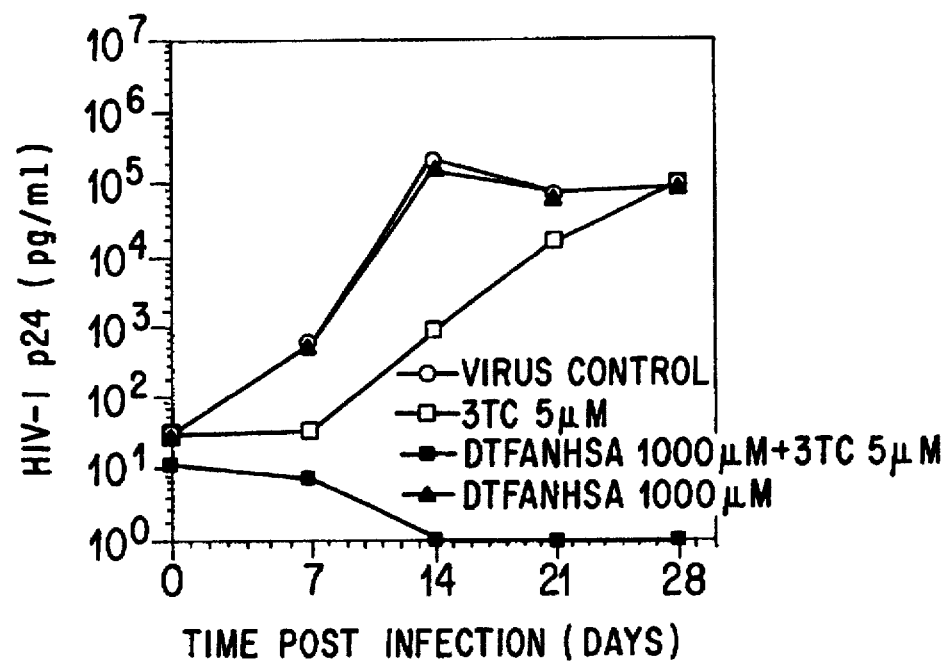

100 μM and 1000 μM DANHSA alone resulted in greater inhibition of viral production than 4 μM AZT alone (see FIGS. 2b, 2c).

The combination of AZT and DANHSA was also studied (see FIGS. 2a, 2b, 2c). At day 7, the 98.2% inhibition of viral production observed with the combination of 1000 μM DANHSA and 4 μM AZT is equivalent to that observed with 1000 μM DANHSA alone compared to infected non-treated control. However, surprisingly, at day 14 the combination of 1000 μM DANHSA and 4 μM AZT resulted in a synergistic inhibitory effect on viral production with 99.997% inhibition.

The combination of ddC and DANHSA which was also studied (see FIGS. 3a, 3b, 3c) synergistically inhibits viral production resulting in the complete elimination of HIV as from day 14 with 1000 μM DANHSA and 0.2 μM ddC.

The combination of ddI and DANHSA which was also studied (see FIGS. 4a, 4b, 4c) synergistically inhibits viral production resulting in the complete elimination of HIV as from day 14 for the three concentrations of DANHSA in combination with 10 μM ddI.

The combination of 3TC and DANHSA which was also studied (see FIGS. 5a, 5b, 5c) inhibits viral production as from day 7 at the three concentrations of DANHSA in combination with 5 μM 3TC and synergistically inhibits viral production resulting in the complete elimination of HIV as from day 14 with DANHSA 100 μM and 1000 μM in combination with 5 μM 3TC.

The new compound DANHSA has been shown to have no cytotoxic effect on a cell population even at very high concentrations as measured by its inhibitory effect on the enzyme ribonucleotide reductase. The inhibition of ribonucleotide reductase was measured by analyzing the concentration of the tyrosine radical. Experiments were conducted using a murine leukemia cell line L1210, transfected for hyperexpression of the R2 sub-unit which has the free radical. The cells which had been treated for 4 to 5 hours with DANHSA were analyzed by electronic paramagnetic resonance (EPR). Under these conditions, a concentration of 4 mM DANHSA was shown to have no inhibitory effect.

Example 2

The anti-viral activity of DTFANHSA alone and in combination with RT inhibitors on non-activated resting human lymphocytes infected with HIV (see Table 2 and FIGS. 6 to 10).

PBMC were incubated with the viral strain HIV-1 Lai for two hours at 37° C. with a multiplicity of infection of $10^4$ $TCID_{50}$ per $10^6$ cells. Unbound virus was then eliminated by two successive washes with culture medium and the cells were seeded at a density of $10^6$ cells/ml in the presence of various drug concentrations. On day 7, supernatant were collected for p24 assay and cells were washed 3 times to remove traces of drug. Cells were then submitted to PHA activation by culture in fresh medium containing PHA (Murex 1 µg/ml) and recombinant IL-2 (Roussel 10 U/ml). After 48 hrs of incubation, cells were washed to remove PHA and resuspended in fresh medium containing IL-2. These cultures were maintained for 3 weeks (days 9 to 28): on days 14, 21 and 28, half of the medium was taken and replaced either by fresh medium containing IL-2 (days 21 and 28) or by PHA-activated PBL from blood of healthy donors in RPMI medium 1640 supplemented with IL-2 on day 14 ($4 \times 10^5$ cells/ml). Supernatant were kept for HIV p24 gag protein ELISA assay (DuPont).

The anti-viral effect of three concentrations of DTFANHSA was studied: 10, 100 and 1000 µM alone and in combination with each of four RT inhibitors as measured by inhibition of viral production compared to infected non-treated controls (see FIGS. 6 to 10).

The combination of the three concentrations of DTFANHSA with 4 µM AZT was studied (see FIGS. 7a, 7b, 7c) and resulted on day 7 in an inhibitory effect on viral production with 96.6 to 96.9% inhibition compared to infected non-treated control, whereas AZT alone resulted in 90.7% inhibition.

The combination of ddC and DTFANHSA which was also studied (see FIGS. 8a, 8b, 8c) inhibits viral production at day 7 at the three concentrations of DTFANHSA in combination with 0.2 µM ddC and synergistically inhibits viral production resulting in the complete elimination of HIV as from day 14 with 1000 µM DTFANHSA in combination with 0.2 µM ddC.

The combination of ddI and DTFANHSA which was also studied (see FIGS. 9a, 9b, 9c) inhibits viral production at day 7 at the three concentrations of DTFANHSA in combination with 10 µM ddI and synergistically inhibits viral production resulting in the complete elimination of HIV at day 28 for the three concentrations of DTFANHSA in combination with 10 µM ddI.

The combination of 3TC and DTFANHSA which was also studied (see FIGS. 10a, 10b, 10c) inhibits viral production as from day 7 at the three concentrations of DTFANHSA in combination with 5 µM 3TC and synergistically inhibits viral production resulting in the complete elimination of HIV as from day 14 with DTFANHSA 100 µM and 1000 µM in combination with 5 µM 3TC.

Example 3

An example of the potential use in treating asthma is presented as follows. A patient suffering from difficulty in breathing was administered 5 ml. of an aqueous solution containing 25 mg. of DANHSA by oral route and within some minutes experienced the effects of broncho-dilation, making his breathing considerably easier.

TABLE 1

Anti-viral activity of DANHSA, AZT, ddC, ddI and 3TC alone and in various combinations in non-activated human peripheral blood mononuclear cells (PBMC) infected with HIV as measured by p24 gag protein expressed in pg/ml.

| Time post infection (days) | Virus control | DANHSA 10 µM | DANHSA 100 µM | DANHSA 1000 µM |
|---|---|---|---|---|
| 0 | 30 | 79 | 79 | 79 |
| 7 | 558 | 11 | 10 | 10 |
| 14 | 199233 | 6949 | 23331 | 6564 |
| 21 | 73433 | 71465 | 55712 | 57200 |
| 28 | 97000 | 63357 | 37999 | 37962 |

| Time post infection (days) | AZT 4 µM | DANHSA 10 µM + AZT 4 µM | DANSAH 100 µM + AZT 4 µM | DANHSA 1000 µM + AZT 4 µM |
|---|---|---|---|---|
| 0 | 30 | 10 | 9 | 17 |
| 7 | 52 | 107 | 24 | 10 |
| 14 | 116466 | 660000 | 42000 | 6 |
| 21 | 63600 | 740000 | 730000 | 360000 |
| 28 | 78000 | 370000 | 450000 | 325000 |

| Time post infection (days) | ddC 0.2 µM | DANHSA 10 µM + ddC 0.2 µM | DANHSA 100 µM + ddC 0.2 µM | DANHSA 1000 µM + ddC 0.2 µM |
|---|---|---|---|---|
| 0 | 30 | 11 | 20 | 15 |
| 7 | 57 | 10 | 8 | 14 |
| 14 | 11900 | 730000 | 139000 | 0 |
| 21 | 204333 | 540000 | 730000 | 0 |
| 28 | 60700 | 340000 | 310000 | 0 |

| Time post infection (days) | ddI 10 µM | DANHSA 10 µM + ddI 10 µM | DANHSA 100 µM + ddI 10 µM | DANHSA 1000 µM + ddI 10 µM |
|---|---|---|---|---|
| 0 | 30 | 10 | 10 | 15 |
| 7 | 32 | 10 | 12 | 10 |

TABLE 1-continued

Anti-viral activity of DANHSA, AZT, ddC, ddI and 3TC alone and in various combinations in non-activated human peripheral blood mononuclear cells (PBMC) infected with HIV as measured by p24 gag protein expressed in pg/ml.

| | | | | |
|---|---|---|---|---|
| 14 | 842 | 0 | 0 | 0 |
| 21 | 16333 | 0 | 0 | 0 |
| 28 | 112266 | 0 | 0 | 0 |

| Time post infection (days) | 3TC 5 µM | DANHSA 10 µM + 3TC 5 µM | DANHSA 100 µM + 3TC 5 µM | DANHSA 1000 µM + 3TC 5 µM |
|---|---|---|---|---|
| 0 | 30 | 15 | 16 | 11 |
| 7 | 32 | 15 | 30 | 7 |
| 14 | 900 | 0 | 0 | 0 |
| 21 | 17000 | 58 | 0 | 0 |
| 28 | 100000 | 0 | 0 | 0 |

TABLE 2

Anit-viral activity of DTFANHSA, AZT, ddC, ddI and 3TC alone and in various combinations in non-activated human peripheral blood mononuclear cells (PBMC) infected with HIV as measured by p24 gag protein expressed in pg/ml.

| Time post infection (days) | Virus control | DTFANHSA 10 µM | DTFANHSA 100 µM | DTFANHSA 1000 µM |
|---|---|---|---|---|
| 0 | 30 | 30 | 30 | 30 |
| 7 | 558 | 550 | 550 | 550 |
| 14 | 199233 | 160000 | 165000 | 150000 |
| 21 | 73433 | 80000 | 80000 | 85000 |
| 28 | 97000 | 90000 | 85000 | 90000 |

| Time post infection (days) | AZT 4 µM | DTFANHSA 10 µM + AZT 4 µM | DTFANHSA 100 µM + AZT 4 µM | DTFANHSA 1000 µM + AZT 4 µM |
|---|---|---|---|---|
| 0 | 30 | 10 | 17 | 13 |
| 7 | 52 | 17 | 19 | 17 |
| 14 | 116466 | 810000 | 5500000 | 140000 |
| 21 | 63600 | 3800000 | 570000 | 640000 |
| 28 | 78000 | 390000 | 520000 | 270000 |

| Time post infection (days) | ddC 0.2 µM | DTFANHSA 10 µM + ddC 0.2 µM | DTFANHSA 100 µM + ddC 0.2 µM | DTFANHSA 1000 µM + ddC 0.2 µM |
|---|---|---|---|---|
| 0 | 30 | 11 | 21 | 13 |
| 7 | 57 | 37 | 17 | 9 |
| 14 | 11900 | 980000 | 300000 | 0 |
| 21 | 204333 | 4300000 | 590000 | 0 |
| 28 | 60700 | 530000 | 570000 | 0 |

| Time post infection (days) | ddI 10 µM | DTFANHSA 10 µM + ddI 10 µM | DTFANHSA 100 µM + ddI 10 µM | DTFANHSA 1000 µM + ddI 10 µM |
|---|---|---|---|---|
| 0 | 30 | 13 | 18 | 12 |
| 7 | 32 | 6 | 7 | 6 |
| 14 | 842 | 0 | 0 | 0 |
| 21 | 16333 | 41 | 0 | 5 |
| 28 | 112266 | 0 | 0 | 0 |

| Time post infection (days) | 3TC 5 µM | DTFANHSA 10 µM + 3TC 5 µM | DTFANHSA 100 µM + 3TC 5 µM | DTFANHSA 1000 µM + 3TC 5 µM |
|---|---|---|---|---|
| 0 | 30 | 15 | 10 | 12 |
| 7 | 32 | 6 | 7 | 7 |
| 14 | 900 | 0 | 0 | 0 |
| 21 | 17000 | 40 | 0 | 0 |
| 28 | 100000 | 0 | 0 | 0 |

The invention has been described with reference to specific and preferred embodiments. It will be recognized by those skilled in the art that numerous changes and substitutions may be made without departing from the spirit and scope of the invention.

What is claimed is:

1. A compound having the following linear or cyclic formulas:

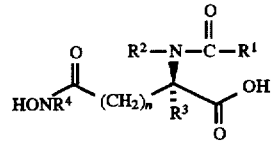

I (linear form)

-continued

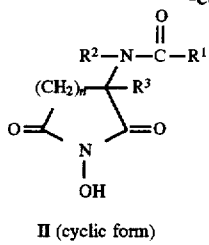

II (cyclic form)

wherein

R¹ is an alkyl group of from 1 to 4 carbon atoms optionally mono-, -di, or tri-substituted with halogen; each of R², R³, and R⁴ is hydrogen, or a straight or branched alkyl radical containing 1 to 8 carbon atoms, an alkenyl radical containing 2 to 8 carbon atoms, an alkynyl radical containing 2 to 8 carbon atoms, a cycloalkyl radical containing 3 to 6 carbon atoms, a cycloalkenyl radical containing from 4 to 6 carbon atoms or a bicycloalkyl radical containing 7 to 11 carbon atoms, these radicals optionally being substituted by at least one substituent selected from halogen, hydroxyl, alkyloxy containing 1 to 4 carbon atoms, dialkyl amino, in which each alkyl contains 1 to 4 carbon atoms, phenyl alkyl in which the alkyl contains 1 to 4 carbon atoms, cyclo alkyl containing 3 to 6 carbon atoms, optionally substituted phenyl, cyano, carboxyl, or alkyloxy carbonyl in which the alkyl contains 1 to 4 carbon atoms; n is an integer from 0 to 6; for formula I and n=1 for formula II and salts thereof.

2. The compound according to claim 1 wherein R¹ is CH₃, each of R², R³, and R⁴ is hydrogen and n is 1.

3. The compound according to claim 1 wherein R¹ is CF₃, each of R², R³, and R⁴ is hydrogen and n is 1.

4. The method of treatment with a compound according to claim 1 to inhibit production or spread of a virus comprising exposing a cell population including said virus to a compound according to claim 1.

5. The method of treatment with a compound according to claim 1 to limit the spread of a virus comprising exposing a cell population including said virus to a compound according to claim 1.

6. The method of treatment with a compound according to claim 1 to block the production of a virus comprising exposing a cell population including said virus to a compound according to claim 1.

7. The method of treatment with a compound according to claim 1 to block the production or limit spread of a virus comprising exposing a cell population including said virus to a synergistic combination of at least one reverse transcriptase inhibitor and at least one compound according to claim 1.

8. The method of treatment with a compound according to claim 1 for inhibiting the spread of a virus comprising exposing a cell population including said virus to a synergistic combination of at least one reverse transcriptase inhibitor and at least one compound according to claim 1.

9. The method of treatment with a compound according to claim 1 to block the production of a virus comprising exposing a cell population including said virus to a synergistic combination of at least one reverse transcriptase inhibitor and at least one compound according to claim 1.

10. The method of claim 4 wherein the virus is a retrovirus.

11. The method of claim 5 wherein the virus is a retrovirus.

12. The method of claim 6 wherein the virus is a retrovirus.

13. The method of claim 7 wherein the virus is a retrovirus.

14. The method of claim 8 wherein the virus is a retrovirus.

15. The method of claim 9 wherein the virus is a retrovirus.

16. The method of claim 4 wherein the virus is HIV-1, HIV-2, HTLV-1, HTLV-2, SIV, HSV, HBV OR HCV.

17. The method of claim 5 wherein the virus is HIV-1, HIV-2, HTLV-1, HTLV-2, SIV, HSV, HBV OR HCV.

18. The method of claim 6 wherein the virus is HIV-1, HIV-2, HTLV-1, HTLV-2, SIV, HSV, HBV OR HCV.

19. The method of claim 7 wherein the virus is HIV-1, HIV-2, HTLV-1, HTLV-2, SIV, HSV, HBV OR HCV.

20. The method of claim 8 wherein the virus is HIV-1, HIV-2, HTLV-1, HTLV-2, SIV, HSV, HBV OR HCV.

21. The method of claim 9 wherein the virus is HIV-1, HIV-2, HTLV-1, HTLV-2, SIV, HSV, HBV OR HCV.

22. The method of claim 4 wherein the compound is D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof.

23. The method of claim 5 wherein the compound is D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof.

24. The method of claim 6 wherein the compound is D-acetamido-N-hydroxy succinamic acid (DANHSA); D-acetamido-N-hydroxy succinimide; D-trifluoroacetamido-N-hydroxy succinamic acid DTFANHSA); D-trifluroacetamido-N-hydroxy succinimide; and salts thereof.

25. The method of claim 7 wherein the compound is D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof and the at least one reverse transcriptase inhibitor is a dideoxynucleoside.

26. The method of claim 8 wherein the compound is D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof; and the at least one reverse transcriptase inhibitor is a dideoxynucleoside.

27. The method of claim 9 wherein the compound is D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof and the at least one reverse transcriptase inhibitor is a dideoxynucleoside.

28. The method of claim 25 wherein the dideoxynucleoside is selected from the group consisting of AZT, ddC, ddA, ddG, ddI, ddT, 3TC and d4T.

29. The method of claim 26 wherein the dideoxynucleoside is selected from the group consisting of AZT, ddC, ddA, ddG, ddI, ddT, 3TC and d4T.

30. The method of claim 27 wherein the dideoxynucleoside is selected from the group consisting of AZT, ddC, ddA, ddG, ddI, ddT, 3TC and d4T.

31. A method of treating HIV infected and AIDS patients comprising administering to the patients a compound of the following linear or cyclic formula:

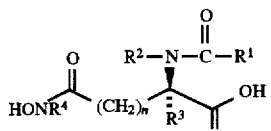

I (linear form)

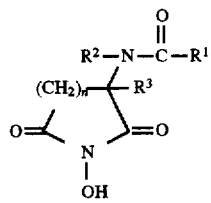

II (cyclic form)

wherein
R$^1$ is an alkyl group of from 1 to 4 carbon atoms optionally mono-, -di, or tri-substituted with halogen; each of R$^2$, R$^3$, and R$^4$ is hydrogen, or a straight or branched alkyl radical containing 1 to 8 carbon atoms, an alkenyl radical containing 2 to 8 carbon atoms, an alkynyl radical containing 2 to 8 carbon atoms, a cycloalkyl radical containing 3 to 6 carbon atoms, a cycloalkenyl radical containing from 4 to 6 carbon atoms or a bicycloalkyl radical containing 7 to 11 carbon atoms, these radicals optionally being substituted by at least one substituent selected from halogen, hydroxyl, alkyloxy containing 1 to 4 carbon atoms, dialkyl amino, in which each alkyl contains 1 to 4 carbon atoms, phenyl alkyl in which the alkyl contains 1 to 4 carbon atoms, cyclo alkyl containing 3 to 6 carbon atoms, optionally substituted phenyl, cyano, carboxyl, or alkyloxy carbonyl in which the alkyl contains 1 to 4 carbon atoms; n is an integer from 0 to 6 for formula I and n=1 for formula II; and salts thereof, in combination with at least one reverse transcriptase inhibitor.

32. The method according to claim 31 wherein the compound is D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof; and the reverse transcriptase inhibitor is a dideoxynucleoside selected from the group consisting of AZT, ddC, ddA, ddG, ddI, ddT, 3TC and d4T.

33. The method of claim 32 wherein the dideoxynucleoside is ddI, AZT, ddC or 3TC.

34. The method of inhibiting or treating Human Immunodeficiency Viruses (HIV) infection, comprising the step of administering to a subject in need thereof an effective amount of a pharmaceutically acceptable composition comprising a synergistic combination of a compound according to claim 1 and at least one reverse transcriptase inhibitor.

35. The method of claim 34 wherein the compound is D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof; and the reverse transcriptase inhibitor is ddI, AZT, ddC or 3TC.

36. The method of inhibiting or blocking Human immunodeficiency Viruses comprising the steps of:

(a) administering to a subject in need thereof an effective amount of a pharmaceutically acceptable composition comprising a compound according to claim 1; and
(b) co-administering an effective amount of a pharmaceutical composition comprising a reverse transcriptase inhibitor.

37. The method of claim 36 wherein the compound is D-acetamido-N-hydroxy succinamic acid (DANHSA); D-acetamido-N-hydroxy succinimide; D-trifluoroacetamido-N-hydroxy succinamic acid (DTFANHSA); D-trifluroacetamido-N-hydroxy succinimide; and salts thereof; and the reverse transcriptase inhibitor is ddI, AZT, ddC or 3TC.

38. The compound according to claim 1 having a cyclic structure wherein R$^1$ is CH$_3$, each R$^2$ and R$^3$ is hydrogen.

39. The compound according to claim 1 having a cyclic structure wherein R$^1$ is CF$_3$, each of R$^2$ and R$^3$ is hydrogen.

40. The compound according to claim 1, wherein said compound is selected from the group consisting of D-acetamido-N-hydroxy succinamic acid (DANHSA), D-acetamido-N-hydroxy succinimide, D-trifluoroacetamido-N-hydroxy succinamic acid (DTFANHSA), D-trifluoroacetamido-N-hydroxy succinimide; and salts thereof.

41. A D-compound of the formulae:

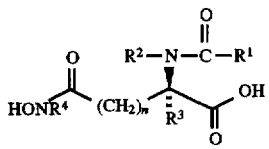

I (linear form)

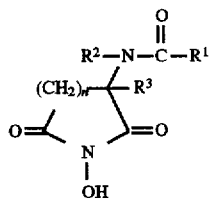

II (cyclic form)

wherein
R$^1$ is an alkyl group of from 1 to 4 carbon atoms optionally mono-, -di, or tri-substituted with halogen; each of R$^2$, R$^3$, and R$^4$ is hydrogen, or a straight or branched alkyl radical containing 1 to 8 carbon atoms, an alkynyl radical containing 2 to 8 carbon atoms, an alkenyl radical containing 2 to 8 carbon atoms, a cycloalkyl radical containing 3 to 6 carbon atoms, a cycloalkenyl radical containing from 4 to 6 carbon atoms or a bicycloalkyl radical containing 7 to 11 carbon atoms, these radicals optionally being substituted by at least one substituent selected from halogen, hydroxyl, alkyloxy containing 1 to 4 carbon atoms, dialkyl amino, in which each alkyl contains 1 to 4 carbon atoms, phenyl alkyl in which the alkyl contains 1 to 4 carbon atoms, cyclo alkyl containing 3 to 6 carbon atoms, optionally substituted phenyl, cyano, carboxyl, or alkyloxy carbonyl in which the alkyl contains 1 to 4 carbon atoms; n is an integer from 0 to 6 for formula I and n=1 for formula II; and salts thereof.

42. A method of treating asthma comprising administering to patients in need of treatment an effective amount of a compound of the following linear or cyclic formula:

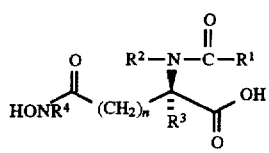

I (linear form)

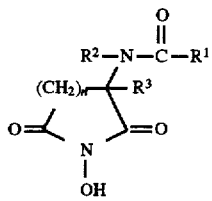

II (cyclic form)

wherein

R¹ is an alkyl group of from 1 to 4 carbon atoms optionally mono-, -di, or tri-substituted with halogen; each of $R^2$, $R^3$, and $R^4$ is hydrogen, or a straight or branched alkyl radical containing 1 to 8 carbon atoms, an alkenyl radical containing 2 to 8 carbon atoms, an alkynyl radical containing 2 to 8 carbon atoms, a cycloalkyl radical containing 3 to 6 carbon atoms, a cycloalkenyl radical containing from 4 to 6 carbon atoms or a bicycloalkyl radical containing 7 to 11 carbon atoms, these radicals optionally being substituted by at least one substituent selected from halogen, hydroxyl, alkyloxy containing 1 to 4 carbon atoms, dialkyl amino, in which each alkyl contains 1 to 4 carbon atoms, phenyl alkyl in which the alkyl contains 1 to 4 carbon atoms, cyclo alkyl containing 3 to 6 carbon atoms, optionally substituted phenyl, cyano, carboxyl, or alkyloxy carbonyl in which the alkyl contains 1 to 4 carbon atoms; n is an integer from 0 to 6 for formula I and n=1 for formula II; and salts thereof.

* * * * *